(12) United States Patent
Suzuki

(10) Patent No.: US 6,558,327 B2
(45) Date of Patent: May 6, 2003

(54) ULTRASONIC DIAGNOSTIC APPARATUS

(75) Inventor: Yoichi Suzuki, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/199,352

(22) Filed: Jul. 19, 2002

(65) Prior Publication Data

US 2003/0032881 A1 Feb. 13, 2003

(30) Foreign Application Priority Data

Jul. 23, 2001 (JP) ........................................ 2001-221051

(51) Int. Cl.[7] .................................................. A61B 8/00
(52) U.S. Cl. .................... 600/443; 600/447; 600/437
(58) Field of Search ............................... 600/443, 447, 600/444, 449, 455, 456, 453, 458, 441, 437

(56) References Cited

U.S. PATENT DOCUMENTS

| | | | | |
|---|---|---|---|---|
| 5,993,391 A | * | 11/1999 | Kamiyama | .................. 600/443 |
| 6,322,510 B1 | * | 11/2001 | Kataoka et al. | ............. 600/453 |
| 6,450,961 B1 | * | 9/2002 | Shiki et al. | ................. 600/458 |

* cited by examiner

*Primary Examiner*—Marvin M. Lateef
*Assistant Examiner*—Maulin Patel
(74) *Attorney, Agent, or Firm*—Carl B. Horton, Esq.; Armstrong Teasdale LLP

(57) ABSTRACT

A photographing cycle including a weak ultrasonic monitor image photographing step of photographing monitor images by using a weak enough ultrasonic wave not to let the contrast agent disappear, a strong ultrasonic B mode image photographing step of photographing a B mode image by using a strong enough ultrasonic wave to make the contrast agent disappear, and a weak ultrasonic CFM image photographing step for photographing CFM images by using a weak enough ultrasonic wave not to let the contrast agent disappear is iterated. The latest image resulting from the addition of the CFM image is displayed superposed over the B mode image.

7 Claims, 21 Drawing Sheets

Ultrasonic diagnostic apparatus

Ultrasonic diagnostic apparatus

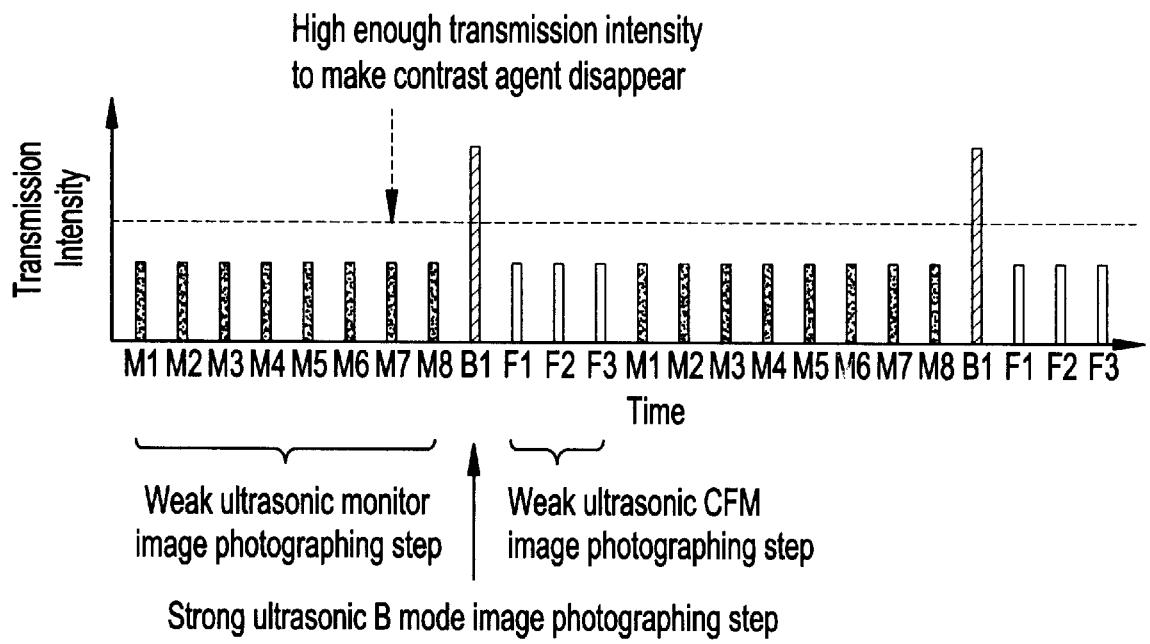
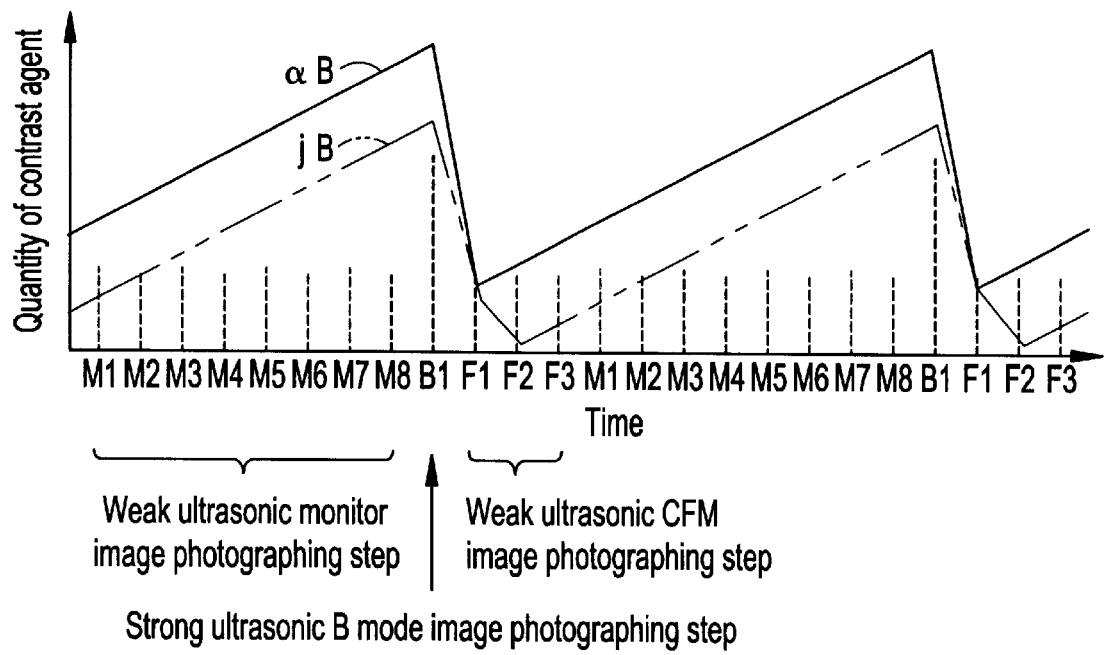

ULTRASONIC DIAGNOSTIC APPARATUS

CROSS REFERENCE TO RELATED APPLICATIONS

This application claims the benefit of Japanese Application No. 2001-221051 filed Jul. 23, 2001.

BACKGROUND OF THE INVENTION

The present invention relates to an ultrasonic scanning method and an ultrasonic diagnostic apparatus, and more particularly to an ultrasonic scanning method and an ultrasonic diagnostic apparatus for eliminating the wasteful use of strong ultrasonic waves irrespective of whether to photograph B mode images or to photograph CFM images and enabling BCFM-based intermittent scanning to be performed more appropriately than according to the related art.

FIG. 19 and FIG. 20 are prior art diagrams illustrating a first example of BCFM-based intermittent scanning performed in an ultrasonic diagnostic apparatus according to the related art.

A photographing cycle including a weak ultrasonic monitor image photographing step of photographing monitor images M1 through M10 by using a weak enough ultrasonic wave not to let the contrast agent (bubbles) disappear, a strong ultrasonic B mode image photographing step of photographing B mode images B1 by using a strong enough ultrasonic wave to make the contrast agent disappear, and a strong ultrasonic CFM (color flow mapping) image photographing step for photographing CFM image F1 by using a strong enough ultrasonic wave to make the contrast agent disappear is iterated.

FIG. 20 is a graph showing variations in the quantity of the contrast agent present in the photographed area.

Incidentally, for the convenience of explanation, it is supposed in this specification that immediately after photographing with strong ultrasonic waves 75% of the contrast agent has disappeared and that and during photographing with weak ultrasonic waves the contrast agent increases (flows in).

As is seen from this graph jB, during the weak ultrasonic monitor image photographing step the contrast agent increases, during the strong ultrasonic B mode image photographing step and the strong ultrasonic CFM image photographing step the contrast agent disappears, and again during the weak ultrasonic monitor image photographing step the contrast agent increases; these variations are repeated.

The latest one of the monitor images M1 through M10 is displayed on, for instance, the left half of the screen.

The monitor images M1 through M10, because of their high frame rate, excel in real time performance. However, their picture quality is poor because they are photographed by using weak ultrasonic waves.

The latest one of B mode images B1 is displayed on, for instance, the right half of the screen.

The picture quality of the B mode images B1 is high, because they are photographed in a state in which the contrast agent has fully infiltrated and by using strong ultrasonic waves. However, because of their low frame rate, they are inferior in real time performance.

The latest one of CFM image F1 is displayed superposed over the B mode image B1.

The picture quality of the CFM image F1 is not so high because they are photographed in a state in which much of the contrast agent has disappeared, but somewhat higher than the monitor images because they are photographed by using strong ultrasonic waves. Because of their low frame rate, they are inferior in real time performance.

FIG. 21 and FIG. 22 are prior art diagrams illustrating a second example of BCFM-based intermittent scanning performed in an ultrasonic diagnostic apparatus according to the related art.

FIG. 21 is a diagram illustrating an ultrasonic scanning method.

A photographing cycle including a weak ultrasonic monitor image photographing step of photographing monitor images M1 through M10 by using a weak enough ultrasonic wave not to let the contrast agent disappear, a strong ultrasonic CFM image photographing step for photographing CFM image F1 by using a strong enough ultrasonic wave to make the contrast agent disappear, and a strong ultrasonic B mode image photographing step of photographing B mode images B1 by using a strong enough ultrasonic wave to make the contrast agent disappear is iterated.

FIG. 22 is a graph showing variations in the quantity of the contrast agent present in the photographed area.

As is seen from this graph jF, during the weak ultrasonic monitor image photographing step the contrast agent increases, during the strong ultrasonic CFM image photographing step and the strong ultrasonic B mode image photographing step the contrast agent disappears, and again during the weak ultrasonic monitor image photographing step the contrast agent increases; these variations are repeated.

The latest one of the monitor images M1 through M10 is displayed on, for instance, the left half of the screen.

The monitor images M1 through M10, because of their high frame rate, excel in real time performance. However, their picture quality is poor because they are photographed by using weak ultrasonic waves.

The latest one of CFM image F1 is displayed on, for instance, the right half of the screen.

The picture quality of the CFM image F1 is high because they are photographed in a state in which the contrast agent has fully infiltrated and by using strong ultrasonic waves. However, because of their low frame rate, they are inferior in real time performance.

The latest one of B mode images B1 is displayed superposed over the CFM mode image F1.

The picture quality of the B mode images B1 is not so high, because they are photographed in a state in which much of the contrast agent has disappeared, but somewhat higher than the monitor images because they are photographed by using strong ultrasonic waves. Because of their low frame rate, they are inferior in real time performance.

FIG. 23 through FIG. 25 are prior art diagrams illustrating a third example of BCFM-based intermittent scanning performed in an ultrasonic diagnostic apparatus according to the related art.

As shown in FIG. 23, a scanned region S is divided into, for instance, four partial regions a through d.

Then, as shown in FIG. 24, a photographing cycle including a weak ultrasonic monitor image photographing step of photographing monitor images M1 through M8 all over the scanned region S by using a weak enough ultrasonic wave not to let the contrast agent disappear, a strong ultrasonic B mode partial photographing step of photographing B mode images B1 in each of the partial regions a, b, c and d by using a strong enough ultrasonic wave to make the contrast agent disappear, and a sequential partial photographic step at which strong ultrasonic CFM image partial photographing steps for sequentially photographing CFM image F1 by using a strong enough ultrasonic wave to make the contrast agent disappear is iterated.

FIG. 25 is a graph showing variations in the quantity of the contrast agent present in the photographed area.

In partial region a, as is seen from graph jpBa, during the weak ultrasonic monitor image photographing step the contrast agent increases, during the strong ultrasonic B mode partial photographing step and the strong ultrasonic CFM image partial photographing step the contrast agent disappears, and again during the weak ultrasonic monitor image photographing step the contrast agent increases; these variations are repeated.

The same is true of graph jpBb of partial region b, graph jpBc of partial region c and graph jpbd of partial region d as of graph jpBa of partial region a.

The latest one of the monitor images M1 through M8 is displayed on, for instance, the left half of the screen.

The monitor images M1 through M8, because of their high frame rate, excel in real time performance. However, their picture quality is poor because they are photographed by using weak ultrasonic waves.

The latest one of B mode images B1 is displayed on, for instance, the right half of the screen.

The picture quality of the B mode images B1 is high, because they are photographed in a state in which the contrast agent has fully infiltrated and by using strong ultrasonic waves. However, because of their low frame rate, they are inferior in real time performance.

The latest one of CFM image F1 is displayed superposed over the B mode image B1.

The picture quality of the CFM image F1 is not so high because they are photographed in a state in which much of the contrast agent has disappeared, but somewhat higher than the monitor images because they are photographed by using strong ultrasonic waves. Because of their low frame rate, they are inferior in real time performance.

FIG. 26 and FIG. 27 are prior art diagrams illustrating a fourth example of BCFM-based intermittent scanning performed in an ultrasonic diagnostic apparatus according to the related art.

As shown in FIG. 26, a photographing cycle including a weak ultrasonic monitor image photographing step of photographing monitor images M1 through M8 all over the scanned region S by using a weak enough ultrasonic wave not to let the contrast agent disappear, a strong ultrasonic CFM monitor image partial photographing step of photographing CFM image F1 in each of the partial regions a, b, c and d by using a strong enough ultrasonic wave to make the contrast agent disappear, and a sequential partial photographic step at which strong ultrasonic B mode image partial photographing steps for sequentially photographing B mode images B1 by using a strong enough ultrasonic wave to make the contrast agent disappear is iterated.

FIG. 27 is a graph showing variations in the quantity of the contrast agent present in the photographed area.

In partial region a, as is seen from graph jpFa, during the weak ultrasonic monitor image photographing step the contrast agent increases, during the strong ultrasonic CFM image partial photographing step and the strong ultrasonic B mode partial photographing step the contrast agent disappears, and again during the weak ultrasonic monitor image photographing step the contrast agent increases; these variations are repeated.

The same is true of graph jpFb of partial region b, graph jpFc of partial region c and graph jpFd of partial region d as of graph jpFa of partial region a.

The latest one of the monitor images M1 through M8 is displayed on, for instance, the left half of the screen.

The monitor images M1 through M8, because of their high frame rate, excel in real time performance. However, their picture quality is poor because they are photographed by using weak ultrasonic waves.

The latest one of CFM image F1 is displayed on, for instance, the right half of the screen.

The picture quality of the CFM image F1 is high because they are photographed in a state in which the contrast agent has fully infiltrated and by using strong ultrasonic waves. However, because of their low frame rate, they are inferior in real time performance.

The latest one of B mode images B1 is displayed superposed over the CFM mode image F1.

The picture quality of the B mode images B1 is not so high, because they are photographed in a state in which much of the contrast agent has disappeared, but somewhat higher than the monitor images because they are photographed by using strong ultrasonic waves. Because of their low frame rate, they are inferior in real time performance.

In the above-described BCFM-based intermittent scanning with the conventional ultrasonic diagnostic apparatus, strong ultrasonic waves are used irrespective of whether to photograph B mode images or to photograph CFM images. However, in the first example of the related art, the picture quality of the B mode image obtained at the strong ultrasonic B mode image photographing step immediately after the weak ultrasonic monitor image photographing step is high, but the picture quality of the CFM image obtained at the following strong ultrasonic CFM image photographing step is not so high. Thus, there is a problem that the use of strong ultrasonic waves at this strong ultrasonic CFM image photographing step scarcely provides any advantage.

Similarly in the second example of the related art, there is a problem that the use of strong ultrasonic waves at the strong ultrasonic B mode image photographing step scarcely provides any advantage.

Similarly in the third example of the related art, there is a problem that the use of strong ultrasonic waves at the strong ultrasonic CFM image partial photographing step scarcely provides any advantage.

Similarly in the fourth example of the related art, there is a problem that the use of strong ultrasonic waves at the strong ultrasonic B mode partial photographing step scarcely provides any advantage.

SUMMARY OF THE INVENTION

An object of the present invention, therefore, is to provide an ultrasonic scanning method and an ultrasonic diagnostic apparatus for eliminating the wasteful use of strong ultrasonic waves irrespective of whether to photograph B mode images or to photograph CFM images and enabling BCFM-based intermittent scanning to be performed more appropriately than according to the related art.

According to its first aspect, the present invention provides an ultrasonic scanning method characterized in that a photographing cycle including a strong ultrasonic B mode image photographing step of photographing B mode images by using a strong enough ultrasonic wave to make a contrast agent disappear, a weak ultrasonic turbulent image photographing step of photographing turbulent images by using a weak enough ultrasonic wave not to let the contrast agent disappear, and a weak ultrasonic monitor image photographing step of repeating many times photographing of monitor images by using a weak enough ultrasonic wave not to let the contrast agent disappear is iterated.

By the ultrasonic scanning method according to the first aspect described above, B mode images are photographed by using a strong ultrasonic wave, and turbulent images (including CFM images) are photographed by using a weak ultrasonic wave. As a result, even during the weak ultrasonic turbulent image photographing step the contrast agent does not disappear, but the quantity of the contrast agent is increased by an inflow. Therefore, if it is assumed that the frame rate is the same as in the above-described first example of the related art, as the quantity of the infiltrating contrast agent is greater than in the first example of the related art, the picture quality of B mode images is improved. Or even if the frame rate is higher than in the first example of the related art, as the quantity of the infiltrating contrast agent can be kept substantially equal to that in the first example of the related art, comparable picture quality can be achieved for B mode images that in the first example of the related art. Thus, the frame rate can be enhanced without sacrificing the picture quality of B mode images. On the other hand, the picture quality of turbulent images is poor because they are photographed by using a weak ultrasonic wave, but it is only slightly poorer than in the first example of the related art. Therefore, as a whole, BCFM-based intermittent scanning can be accomplished more appropriately than by the first example of the related art.

According to its second aspect, the invention provides an ultrasonic scanning method characterized in that, in the ultrasonic scanning method of the above-described configuration, either the strong ultrasonic B mode image photographing step, the weak ultrasonic turbulent image photographing step and the weak ultrasonic monitor image photographing step are executed in this order, or the strong ultrasonic B mode image photographing step, the weak ultrasonic monitor image photographing step and the weak ultrasonic turbulent image photographing step are executed in this order.

By the ultrasonic scanning method according to the second aspect described above, the sequence of executing the strong ultrasonic B mode image photographing step, the weak ultrasonic turbulent image photographing step and the weak ultrasonic monitor image photographing step can be selected as desired. This is because a weak ultrasonic wave is used for the photographing of turbulent images, and accordingly its replacement by the photographing of monitor images in the sequence makes no trouble.

According to its third aspect, the invention provides an ultrasonic scanning method characterized in that a photographing cycle including a strong ultrasonic turbulent image photographing step of photographing turbulent images by using a strong enough ultrasonic wave to make a contrast agent disappear, a weak ultrasonic B mode image photographing step of photographing B mode images by using a weak enough ultrasonic wave not to let the contrast agent disappear, and a weak ultrasonic monitor image photographing step of repeating many times photographing of monitor images by using a weak enough ultrasonic wave not to let the contrast agent disappear is iterated.

By the ultrasonic scanning method according to the third aspect described above, only turbulent images are photographed by using a strong ultrasonic wave, and B mode images are photographed by using a weak ultrasonic wave. As a result, even during the weak ultrasonic B mode image photographing step, the contrast agent does not disappear, but the quantity of the contrast agent is increased by an inflow. Therefore, if it is assumed that the frame rate is the same as in the above-described second example of the related art, as the quantity of the infiltrating contrast agent is greater than in the second example of the related art, the picture quality of turbulent images is improved. Or even if the frame rate is higher than in the second example of the related art, as the quantity of the infiltrating contrast agent can be kept substantially equal to that in the second example of the related art, comparable picture quality can be achieved for turbulent images that in the second example of the related art. Thus, the frame rate can be enhanced without sacrificing the picture quality of turbulent images. On the other hand, the picture quality of B mode images is poor because they are photographed by using a weak ultrasonic wave, but it is only slightly poorer than in the second example of the related art. Therefore, as a whole, BCFM-based intermittent scanning can be accomplished more appropriately than by the second example of the related art.

According to its fourth aspect, the invention provides an ultrasonic scanning method characterized in that, in the ultrasonic scanning method of the above-described configuration, either the strong ultrasonic turbulent image photographing step, the weak ultrasonic B mode image photographing step and the weak ultrasonic monitor image photographing step are executed in this order, or the strong ultrasonic turbulent image photographing step, the weak ultrasonic monitor image photographing step and the weak ultrasonic B mode image photographing step are executed in this order.

By the ultrasonic scanning method according to the fourth aspect described above, the sequence of executing the strong ultrasonic wave photographing step, the weak ultrasonic B mode image photographing step and the weak ultrasonic monitor image photographing step can be selected as desired. This is because a weak ultrasonic wave is used for the photographing of B mode images, and accordingly its replacement by the photographing of monitor images in the sequence makes no trouble.

According to its fifth aspect, the invention provides an ultrasonic scanning method characterized in that a change-over is done as designated by the operator between the ultrasonic scanning method according to the above-described first or second aspect and the ultrasonic scanning method according to the third or fourth aspect.

By the ultrasonic scanning method according to the fifth aspect described above, if the ultrasonic scanning method according to the first or second aspect is designated, B mode images of higher picture quality can be obtained, of if the ultrasonic scanning method according to the third or fourth aspect is designated, turbulent images of higher picture quality can be obtained.

According to its sixth aspect, the invention provides an ultrasonic scanning method characterized in that a photographing cycle including a sequential partial photographic step at which a scanned region is divided into two or more partial regions and a strong ultrasonic B mode partial photographing step of photographing in one partial region B mode images by using a strong enough ultrasonic wave to make the contrast agent disappear and a weak ultrasonic turbulent image partial photographing step for photographing turbulent images by using a weak enough ultrasonic wave not to let the contrast agent disappear are sequentially done for each partial region, and of a weak ultrasonic monitor image photographing step of repeating many times photographing of monitor images in the whole scanned region by using a weak enough ultrasonic wave not to let the contrast agent disappear is iterated.

By the ultrasonic scanning method according to the sixth aspect described above, though photographing of B mode images in one partial region and photographing of turbulent images are sequentially repeated for each partial region, it is basically the same in other respects as the ultrasonic scanning method according to the first aspect described above.

Thus, only B mode images are photographed by using a strong ultrasonic wave, and turbulent images are photographed by using a weak ultrasonic wave. As a result, even during the weak ultrasonic turbulent image partial photographing step, the contrast agent does not disappear, but the quantity of the contrast agent is increased by an inflow. Therefore, if it is assumed that the frame rate is the same as in the above-described third example of the related art, as the quantity of the infiltrating contrast agent is greater than in the third example of the related art, the picture quality of B mode images is improved. Or even if the frame rate is higher than in the third example of the related art, as the quantity of the infiltrating contrast agent can be kept substantially equal to that in the third example of the related art, comparable picture quality can be achieved for B mode images that in the third example of the related art. Thus, the frame rate can be enhanced without sacrificing the picture quality of B mode images. On the other hand, the picture quality of turbulent images is poor because they are photographed by using a weak ultrasonic wave, but it is only slightly poorer than in the third example of the related art. Therefore, as a whole, BCFM-based intermittent scanning can be accomplished more appropriately than by the third example of the related art.

According to its seventh aspect, the invention provides an ultrasonic scanning method characterized in that, in the ultrasonic scanning method of the above-described configuration, in one partial region either the strong ultrasonic B mode partial photographing step and the weak ultrasonic turbulent image photographing step are executed in this order or the weak ultrasonic turbulent image photographing step and the strong ultrasonic B mode partial photographing step are executed in this order.

By the ultrasonic scanning method according to the seventh aspect described above, the sequence of executing the strong ultrasonic B mode partial photographing step and the weak ultrasonic turbulent image partial photographing step can be selected as desired. This is because a weak ultrasonic wave is used for the photographing of turbulent images, and accordingly its execution in any position causes no trouble to the photographing of B mode images.

According to its eighth aspect, the invention provides an ultrasonic scanning method characterized in that a photographing cycle including a sequential partial photographic step at which a scanned region is divided into two or more partial regions, and a strong ultrasonic turbulent image partial photographing step of photographing turbulent images in one partial region by using a strong enough ultrasonic wave to make the contrast agent disappear and a weak ultrasonic B mode image partial photographing step of photographing B mode images by using a weak enough ultrasonic wave not to let the contrast agent disappear are sequentially done for each partial region, and of a weak ultrasonic monitor image photographing step of repeating many times photographing of monitor images by using a weak enough ultrasonic wave not to let the contrast agent disappear is iterated.

By the ultrasonic scanning method according to the eighth aspect described above, though photographing of turbulent images in one partial region and photographing of B mode images are sequentially repeated for each partial region, it is basically the same in other respects as the ultrasonic scanning method according to the third aspect described above.

Thus, only turbulent images are photographed by using a strong ultrasonic wave, and B mode images are photographed by using a weak ultrasonic wave. As a result, even during the weak ultrasonic B mode image partial photographing step, the contrast agent does not disappear, but the quantity of the contrast agent is increased by an inflow. Therefore, if it is assumed that the frame rate is the same as in the above-described fourth example of the related art, as the quantity of the infiltrating contrast agent is greater than in the fourth example of the related art, the picture quality of turbulent images is improved. Or even if the frame rate is higher than in the fourth example of the related art, as the quantity of the infiltrating contrast agent can be kept substantially equal to that in the fourth example of the related art, comparable picture quality can be achieved for turbulent images that in the fourth example of the related art. Thus, the frame rate can be enhanced without sacrificing the picture quality of turbulent images. On the other hand, the picture quality of B mode images is poor because they are photographed by using a weak ultrasonic wave, but it is only slightly poorer than in the fourth example of the related art. Therefore, as a whole, BCFM-based intermittent scanning can be accomplished more appropriately than by the fourth example of the related art.

According to its ninth aspect, the invention provides an ultrasonic scanning method characterized in that, in the ultrasonic scanning method of the above-described configuration, either in one partial region the strong ultrasonic turbulent image partial photographing step and the weak ultrasonic B mode image partial photographing step are executed in this order or the weak ultrasonic B mode image partial photographing step and the strong ultrasonic turbulent image partial photographing step are executed in this order.

By the ultrasonic scanning method according to the seventh aspect described above, the sequence of executing the strong ultrasonic turbulent image partial photographing step and the weak ultrasonic B mode image partial photographing step can be selected as desired. This is because a weak ultrasonic wave is used for the photographing of B mode images, and accordingly its execution in any position causes no trouble to the photographing of turbulent images.

According to its 10th aspect, the invention provides an ultrasonic scanning method characterized in that a changeover is done as designated by the operator between the ultrasonic scanning method according to the above-described sixth or seventh aspect and the ultrasonic scanning method according to the eighth or ninth aspect.

By the ultrasonic scanning method according to the 10th aspect described above, if the ultrasonic scanning method according to the sixth or seventh aspect is designated, B mode images of higher picture quality can be obtained, of if the ultrasonic scanning method according to the eighth or ninth aspect is designated, turbulent images of higher picture quality can be obtained.

According to its 11th aspect, the invention provides an ultrasonic scanning method characterized in that, in the ultrasonic scanning method of the above-described configuration, when photographing is done by using a weak enough ultrasonic wave not to let the contrast agent disappear, a higher frequency is used than that when photographing is done by using a strong enough ultrasonic wave to make the contrast agent disappear.

By the ultrasonic scanning method according to the 11th aspect described above, because the frequency of the ultrasonic wave is raised when photographing is done by using a weak ultrasonic wave, the destruction of the contrast agent can be restrained more.

According to its 12th aspect, the invention provides an ultrasonic diagnostic apparatus comprising an ultrasonic probe, an ultrasonic scanning means for scanning the inside of a subject by using that ultrasonic probe, an ultrasonic image generating means for generating an ultrasonic image on the basis of data obtained by scanning, and an ultrasonic image display means for displaying the ultrasonic image, characterized in that the ultrasonic scanning means iterates a photographing cycle including a strong ultrasonic B mode image photographing step of photographing B mode images by using a strong enough ultrasonic wave to make a contrast agent disappear, a weak ultrasonic turbulent image photographing step of photographing turbulent images by using a weak enough ultrasonic wave not to let the contrast agent disappear, and a weak ultrasonic monitor image photographing step of repeating many times photographing of monitor images by using a weak enough ultrasonic wave not to let the contrast agent disappear.

With the ultrasonic diagnostic apparatus according to the 12th aspect described above, the ultrasonic scanning method according to the first aspect described above can be carried out appropriately.

According to its 13th aspect, the invention provides an ultrasonic diagnostic apparatus characterized in that, in the ultrasonic diagnostic apparatus of the above-described configuration, the ultrasonic scanning means either executes the strong ultrasonic B mode image photographing step, the weak ultrasonic turbulent image photographing step and the weak ultrasonic monitor image photographing step in this order or executes the strong ultrasonic B mode image photographing step, the weak ultrasonic monitor image photographing step and the weak ultrasonic turbulent image photographing step in this order.

With the ultrasonic diagnostic apparatus according to the 13th aspect described above, the ultrasonic scanning method according to the second aspect described above can be carried out appropriately.

According to its 14th aspect, the invention provides an ultrasonic diagnostic apparatus provided with an ultrasonic probe, an ultrasonic scanning means for scanning the inside of a subject by using that ultrasonic probe, an ultrasonic image generating means for generating an ultrasonic image on the basis of data obtained by scanning, and an ultrasonic image display means for displaying the ultrasonic image, characterized in that the ultrasonic scanning means iterates a photographing cycle including a strong ultrasonic turbulent image photographing step of photographing turbulent images by using a strong enough ultrasonic wave to make a contrast agent disappear, a weak ultrasonic B mode image photographing step of photographing B mode images by using a weak enough ultrasonic wave not to let the contrast agent disappear, and a weak ultrasonic monitor image photographing step of repeating many times photographing of monitor images by using a weak enough ultrasonic wave not to let the contrast agent disappear.

With the ultrasonic diagnostic apparatus according to the 14th aspect described above, the ultrasonic scanning method according to the third aspect described above can be carried out appropriately.

According to its 15th aspect, the invention provides an ultrasonic diagnostic apparatus characterized in that, in the ultrasonic diagnostic apparatus of the above-described configuration, the ultrasonic scanning means either executes the strong ultrasonic turbulent image photographing step, the weak ultrasonic B mode image photographing step and the weak ultrasonic monitor image photographing step in this order or the strong ultrasonic turbulent image photographing step, the weak ultrasonic monitor image photographing step and the weak ultrasonic B mode image photographing step in this order.

With the ultrasonic diagnostic apparatus according to the 15th aspect described above, the ultrasonic scanning method according to the fourth aspect described above can be carried out appropriately.

According to its 16th aspect, the invention provides an ultrasonic diagnostic apparatus provided with the ultrasonic scanning means according to the 12th or 13th aspect and the ultrasonic scanning means according to the 14th or 15th aspect, and with a designating means for use by the operator to designate the ultrasonic scanning means to be worked.

With the ultrasonic diagnostic apparatus according to the 16th aspect described above, the ultrasonic scanning method according to the fifth aspect described above can be carried out appropriately.

According to its 17th aspect, the invention provides an ultrasonic diagnostic apparatus provided with an ultrasonic probe, an ultrasonic scanning means for scanning the inside of a subject by using that ultrasonic probe, an ultrasonic image generating means for generating an ultrasonic image on the basis of data obtained by scanning, and an ultrasonic image display means for displaying the ultrasonic image, characterized in that the ultrasonic scanning means iterates a photographing cycle including a sequential partial photographic step at which a scanned region is divided into two or more partial regions and a strong ultrasonic B mode partial photographing step of photographing in one partial region B mode images by using a strong enough ultrasonic wave to make the contrast agent disappear and a weak ultrasonic turbulent image partial photographing step for photographing turbulent images by using a weak enough ultrasonic wave not to let the contrast agent disappear are sequentially done for each partial region, and of a weak ultrasonic monitor image photographing step of repeating many times photographing of monitor images in the whole scanned region by using a weak enough ultrasonic wave not to let the contrast agent disappear.

With the ultrasonic diagnostic apparatus according to the 17th aspect described above, the ultrasonic scanning method according to the sixth aspect described above can be carried out appropriately.

According to its 18th aspect, the invention provides an ultrasonic diagnostic apparatus characterized in that, in the ultrasonic diagnostic apparatus of the above-described configuration, the ultrasonic scanning means executes in one partial region either the strong ultrasonic B mode partial photographing step and the weak ultrasonic turbulent image photographing step in this order or the weak ultrasonic turbulent image photographing step and the strong ultrasonic B mode partial photographing step in this order.

With the ultrasonic diagnostic apparatus according to the 18th aspect described above, the ultrasonic scanning method according to the seventh aspect described above can be carried out appropriately.

According to its 19th aspect, the invention provides an ultrasonic diagnostic apparatus provided with an ultrasonic probe, an ultrasonic scanning means for scanning the inside of a subject by using that ultrasonic probe, an ultrasonic image generating means for generating an ultrasonic image on the basis of data obtained by scanning, and an ultrasonic image display means for displaying the ultrasonic image, characterized in that the ultrasonic scanning means iterates a photographing cycle including a sequential partial photographic step at which a scanned region is divided into two or more partial regions, and a strong ultrasonic turbulent image partial photographing step of photographing turbulent images in one partial region by using a strong enough ultrasonic wave to make the contrast agent disappear and a weak ultrasonic B mode image partial photographing step of photographing B mode images by using a weak enough ultrasonic wave not to let the contrast agent disappear are sequentially done for each partial region, and of a weak ultrasonic monitor image photographing step of repeating many times photographing of monitor images in the whole scanned region by using a weak enough ultrasonic wave not to let the contrast agent disappear.

With the ultrasonic diagnostic apparatus according to the 19th aspect described above, the ultrasonic scanning method according to the eighth aspect described above can be carried out appropriately.

According to its 20th aspect, the invention provides an ultrasonic diagnostic apparatus characterized in that, in the ultrasonic diagnostic apparatus of the above-described configuration, the ultrasonic scanning means executes in one partial region either the strong ultrasonic wave photographing step and the weak ultrasonic B mode image photographing step in this order or the weak ultrasonic B mode image photographing step and the strong ultrasonic wave photographing step in this order.

With the ultrasonic diagnostic apparatus according to the 20th aspect described above, the ultrasonic scanning method according to the ninth aspect described above can be carried out appropriately.

According to its 21st aspect, the invention provides an ultrasonic diagnostic apparatus provided with the ultrasonic scanning means according to the 17th or 18th aspect and the ultrasonic scanning means stated according to the 19 or 20th aspect, and with a designating means for use by the operator to designate the ultrasonic scanning means to be worked.

With the ultrasonic diagnostic apparatus according to the 21st aspect described above, the ultrasonic scanning method according to the 10th aspect described above can be carried out appropriately.

According to its 22nd aspect, the invention provides an ultrasonic diagnostic apparatus characterized in that, in the ultrasonic diagnostic apparatus of the above-described configuration, the ultrasonic scanning means uses a higher frequency when photographing is done by using a weak enough ultrasonic wave not to let the contrast agent disappear than that when photographing is done by using a strong enough ultrasonic wave to make the contrast agent disappear.

With the ultrasonic diagnostic apparatus according to the 22nd aspect described above, the ultrasonic scanning method according to the 11th aspect described above can be carried out appropriately.

Therefore, the ultrasonic scanning method and the ultrasonic diagnostic apparatus according to the present invention make it possible to carry out BCFM-based intermittent scanning more appropriately than the related art and eliminating the wasteful use of a strong ultrasonic wave whether B mode images are to be photographed of CFM images are to be photographed.

Further objects and advantages of the present invention will be apparent from the following description of the preferred embodiments of the invention as illustrated in the accompanying drawings.

BRIEF DESCRIPTION OF THE DRAWINGS

FIG. 2 is a diagram illustrating a first ultrasonic scanning method pertaining to the invention.

FIG. 3 is a graph showing variations in the quantity of the contrast agent in the first ultrasonic scanning method pertaining to the invention.

DETAILED DESCRIPTION OF THE INVENTION

The present invention will be described in detail with reference to modes of carrying it out illustrated in drawings.

Figure 1:
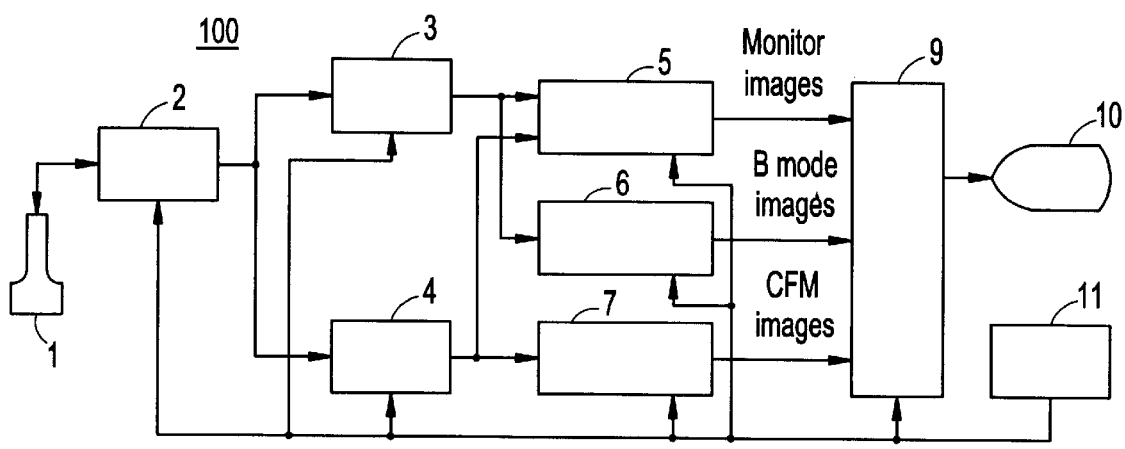
FIG. 1 is a diagram illustrating the configuration of an ultrasonic diagnostic apparatus pertaining to one mode of implementing the present invention.

FIG. 1 illustrates the configuration of an ultrasonic diagnostic apparatus pertaining to one mode of implementing the present invention.

This ultrasonic waves diagnostic apparatus 100 is configured of an ultrasonic probe 1; a transmitting/receiving section 2 for transmitting a strong enough ultrasonic wave to make the contrast agent disappear or a weak enough ultrasonic wave not to let the contrast agent disappear, receiving an echo corresponding to it and outputting a reception signal; a B mode processing section 3 for generating B mode image information from the reception signal; a CFM processing section 4 for generating CFM image information from the reception signal; a monitor image generating section 5 for selecting either B mode image information obtained by scanning with a weak enough ultrasonic wave not to let the contrast agent disappear or CFM image information obtained by-scanning with a weak enough ultrasonic wave not to let the contrast agent disappear and generating monitor images; a B mode image generating section 6 for generating B mode images from B mode image information obtained by scanning with a strong enough ultrasonic wave to make the contrast agent disappear; a CFM image generating section 7 for generating CFM images from CFM image information obtained by scanning with a strong enough ultrasonic wave to make the contrast agent disappear; a display control section 9 for performing control to display a monitor image on the left half of the screen of a display unit 10 and to display an synthetic image synthesized by having a B mode image and a CFM image overlap each other on the right half of the screen of the display unit 10; the display unit 10 for displaying images and messages; and a scan control section 11 for controlling overall operations.

The ultrasonic diagnostic apparatus 100 executes an ultrasonic scanning method illustrated in FIG. 2, FIG. 4, FIG. 6, FIG. 8, FIG. 11, FIG. 13, FIG. 15 or FIG. 17 by injecting a contrast agent into the blood flow of a subject, and working the ultrasonic probe 1, the transmitting/receiving section 2, the B mode processing section 3 and the CFM processing section 4 under the control of the scan control section 11. The operator designates which of the ultrasonic scanning methods illustrated in FIG. 2, FIG. 4, FIG. 6, FIG. 8, FIG. 11, FIG. 13, FIG. 15 and FIG. 17 is to be executed.

First Ultrasonic Scanning Method

As shown in FIG. 2, a photographing cycle including a weak ultrasonic monitor image photographing step of photographing monitor images M1 through M8 by using a weak enough ultrasonic wave not to let the contrast agent disappear, a strong ultrasonic B mode image photographing step of photographing a B mode image B1 by using a strong enough ultrasonic wave to make the contrast agent disappear, and a weak ultrasonic CFM image photographing step for photographing CFM images F1 through F3 by using a weak enough ultrasonic wave not to let the contrast agent disappear is iterated.

The latest image ΣF resulting from the addition of the CFM image F1 through F3 is displayed superposed over the B mode image B1.

FIG. 3 is a graph showing variations in the quantity of the contrast agent present in the photographed area.

As is seen from this graph αB, during the weak ultrasonic monitor image photographing step the contrast agent increases, and during the strong ultrasonic B mode image photographing step the contrast agent disappears. After that, during the weak ultrasonic CFM image photographing step and the weak ultrasonic monitor image photographing step the contrast agent increases, and during the strong ultrasonic B mode image photographing step the contrast agent disappears; these variations are repeated.

As comparison of this graph aB and graph jB in the first example of the related art described above would reveal, supposing that the frame rate is the same as in the first example of the related art, the quantity of the contrast agent during the photographing of the B mode image is greater than in the first example of the related art. As a result, the picture quality of the B mode image can be improved. In other words, even if the frame rate is higher than in the first example of the related art, the quantity of the contrast agent can be kept about the same, and therefore comparable picture quality of the B mode image to that in the first example of the related art can be achieved. Thus, without sacrificing the picture quality of the B mode image, the frame rate can be raised.

The picture quality of CFM images ΣF is not so high, but on account of the photographing in a state in which much of the contrast agent has disappeared and the use of a weak ultrasonic wave, their addition results in a comparable quality level to that in the first example of the related art.

Incidentally, although the picture quality of the CFM image F1 is rather poor on account of the photographing in a state in which much of the contrast agent has disappeared and the use of a weak ultrasonic wave, it is only slightly poorer than in the first example of the related art, only the CFM image F1 can as well be used instead of using the added CFM images ΣF.

By the first ultrasonic scanning method so far described, BCFM-based intermittent scanning can be accomplished generally more appropriately than by the first example of the related art. Moreover it is appropriate for the observation of opacification in B mode images, and can also provide information on blood flow in the surroundings through CFM images.

Second Ultrasonic Scanning Method

Figure 4:
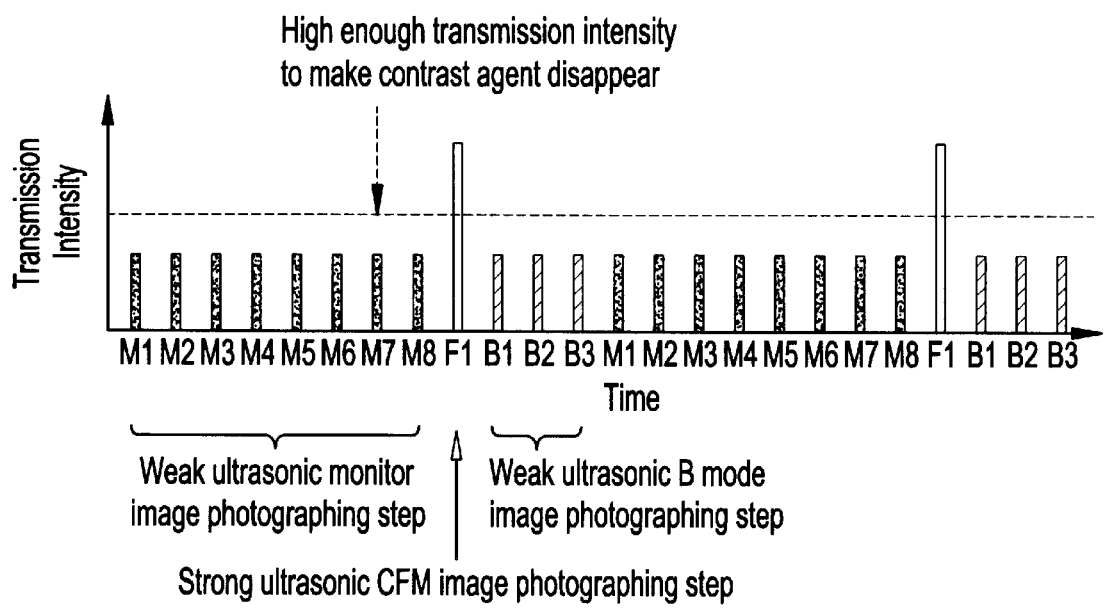
FIG. 4 is a diagram illustrating a second ultrasonic scanning method pertaining to the invention.

As shown in FIG. 4, a photographing cycle including a weak ultrasonic monitor image photographing step of photographing monitor images M1 through M8 by using a weak enough ultrasonic wave not to let the contrast agent disappear, a strong ultrasonic CFM image photographing step for photographing CFM image F1 by using a strong enough ultrasonic wave to make the contrast agent disappear, and a weak ultrasonic B mode image photographing step of photographing B mode images B1 through B3 by using a weak enough ultrasonic wave not to let the contrast agent disappear is iterated.

The latest image ΣB resulting from the addition of the B mode images B1 through B3 is displayed superposed over the CFM image F1.

Figure 5:
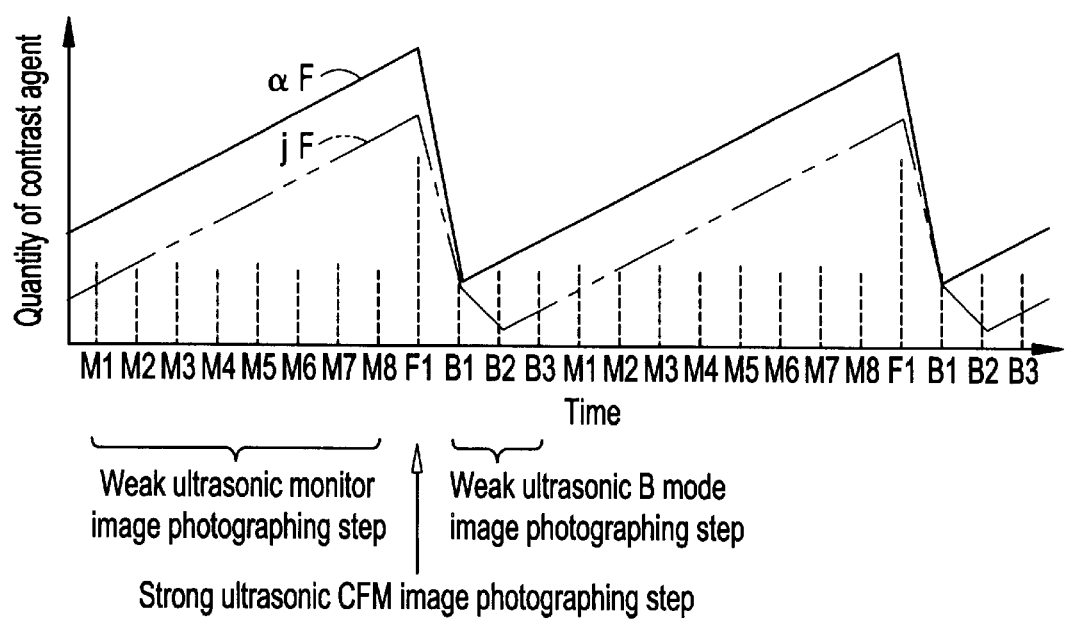
FIG. 5 is a graph showing variations in the quantity of the contrast agent in the second ultrasonic scanning method pertaining to the invention.

FIG. 5 is a graph showing variations in the quantity of the contrast agent present in the photographed area.

As is seen from this graph αF, during the weak ultrasonic monitor image photographing step the contrast agent increases, and during the strong ultrasonic CFM image photographing step the contrast agent disappears. After that, during the weak ultrasonic B mode image photographing step and the weak ultrasonic monitor image photographing step the contrast agent increases, and during the strong ultrasonic CFM image photographing step the contrast agent disappears; these variations are repeated.

As comparison of this graph αF and graph jF in the second example of the related art described above would reveal, supposing that the frame rate is the same as in the second example of the related art, the quantity of the contrast agent during the photographing of the CFM image is greater than in the second example of the related art. As a result, the picture quality of the CFM image can be improved. In other words, even if the frame rate is higher than in the second example of the related art, the quantity of the contrast agent can be kept about the same, and therefore comparable picture quality of the CFM image to that in the second example of the related art can be achieved. Thus, without sacrificing the picture quality of the CFM image, the frame rate can be raised.

The picture quality of B mode images ΣB is not so high, but on account of the photographing in a state in which much of the contrast agent has disappeared and the use of a weak ultrasonic wave, their addition results in a comparable quality level to that in the second example of the related art.

Incidentally, although the picture quality of the B mode image B1 is rather poor on account of the photographing in a state in which much of the contrast agent has disappeared and the use of a weak ultrasonic wave, it is only slightly poorer than in the second example of the related art, only the B mode image B1 can as well be used instead of using the added B mode images ΣB.

By the second ultrasonic scanning method so far described, BCFM-based intermittent scanning can be accomplished generally more appropriately than by the second example of the related art. Moreover it is appropriate for the observation of opacification in CFM images, and can also provide structural information through B mode images.

Third Ultrasonic Scanning Method

A third ultrasonic scanning method is a variation of the first ultrasonic scanning method in which the order of the relative positions of the strong ultrasonic B mode image photographing step and the weak ultrasonic CFM image photographing step are changed.

Figure 6:
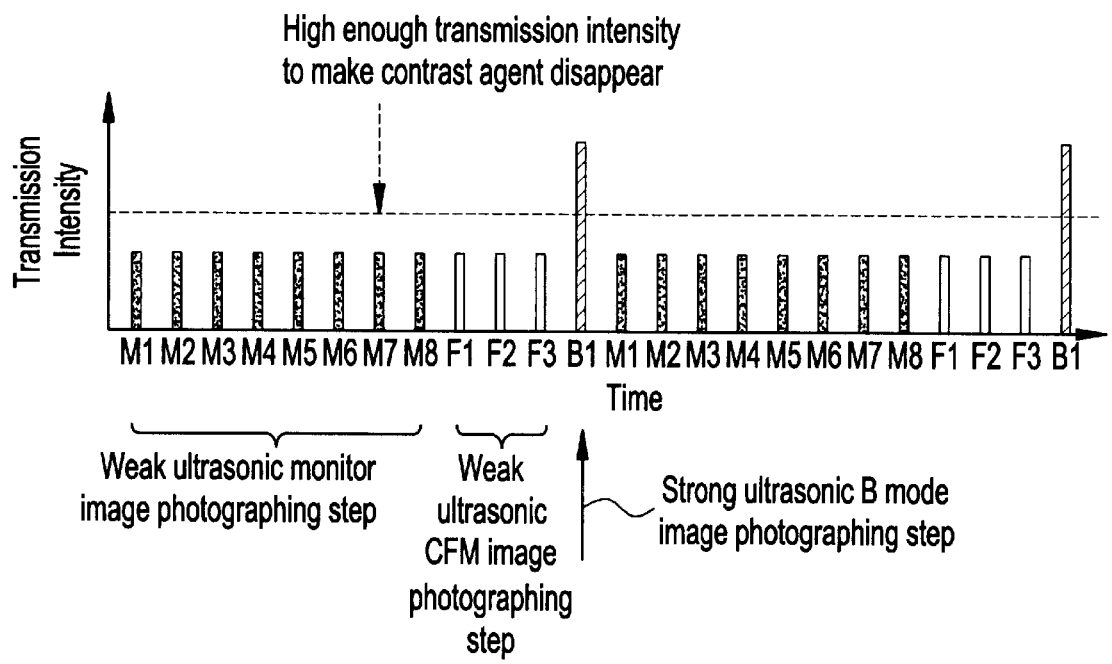
FIG. 6 is a diagram illustrating a third ultrasonic scanning method pertaining to the invention.

As shown in FIG. 6, the weak ultrasonic CFM image photographing step is executed immediately after the weak ultrasonic monitor image photographing step, followed by the execution of the strong ultrasonic B mode image photographing step.

Figure 7:
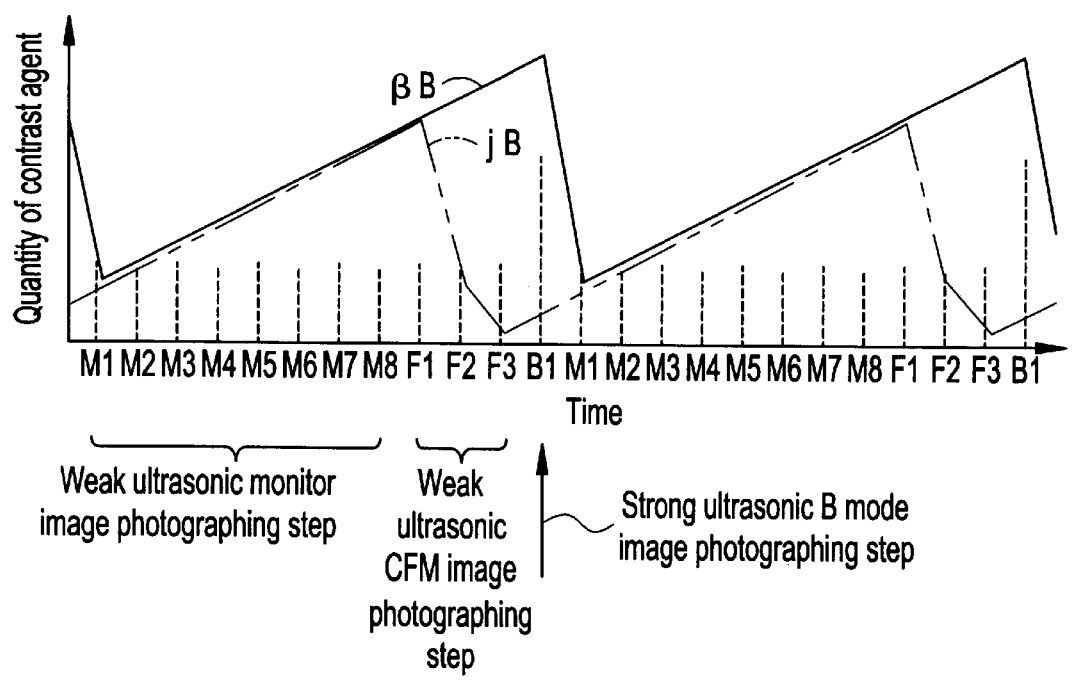
FIG. 7 is a graph showing variations in the quantity of the contrast agent in the third ultrasonic scanning method pertaining to the invention.

As is seen from graph βB in FIG. 7, during the weak ultrasonic monitor image photographing step and the weak ultrasonic CFM image photographing step the contrast agent increases, during the strong ultrasonic B mode image photographing step the contrast agent disappears, during the weak ultrasonic monitor image photographing step and the weak ultrasonic CFM image photographing step the contrast agent increases; these variations are repeated.

As comparison of this graph βB and graph jB in the first example of the related art described above would reveal, supposing that the frame rate is the same as in the first example of the related art, the quantity of the contrast agent during the photographing of the B mode image is greater than in the first example of the related art. As a result, the picture quality of the B mode image can be improved. In other words, even if the frame rate is higher than in the first example of the related art, the quantity of the contrast agent can be kept about the same, and therefore comparable picture quality of the B mode image to that in the first example of the related art can be achieved. Thus, without sacrificing the picture quality of the B mode image, the frame rate can be raised.

The picture quality of the CFM images ΣF is not so high, because of the use of a weak ultrasonic wave in photographing, but the photographing in a state in which the contrast agent has increased and the addition of a plurality of CFM images result in a comparable quality level to that in the first example of the related art.

Incidentally, although the picture quality of the CFM image F1 is rather poor on account of the use of a weak ultrasonic wave in, it is only slightly poorer than in the first example of the related art, only the CFM image F1 can as well be used instead of using the added CFM images ΣF.

By the third ultrasonic scanning method so far described, BCFM-based intermittent scanning can be accomplished generally more appropriately than by the first example of the related art. Moreover it is appropriate for the observation of opacification in B mode images, and can also provide information on blood flow in the surroundings through CFM images.

Fourth Ultrasonic Scanning Method

A fourth ultrasonic scanning method is a variation of the second ultrasonic scanning method in which the order of the relative positions of the strong ultrasonic CFM image photographing step and the weak ultrasonic B mode image photographing step are changed.

Figure 8:
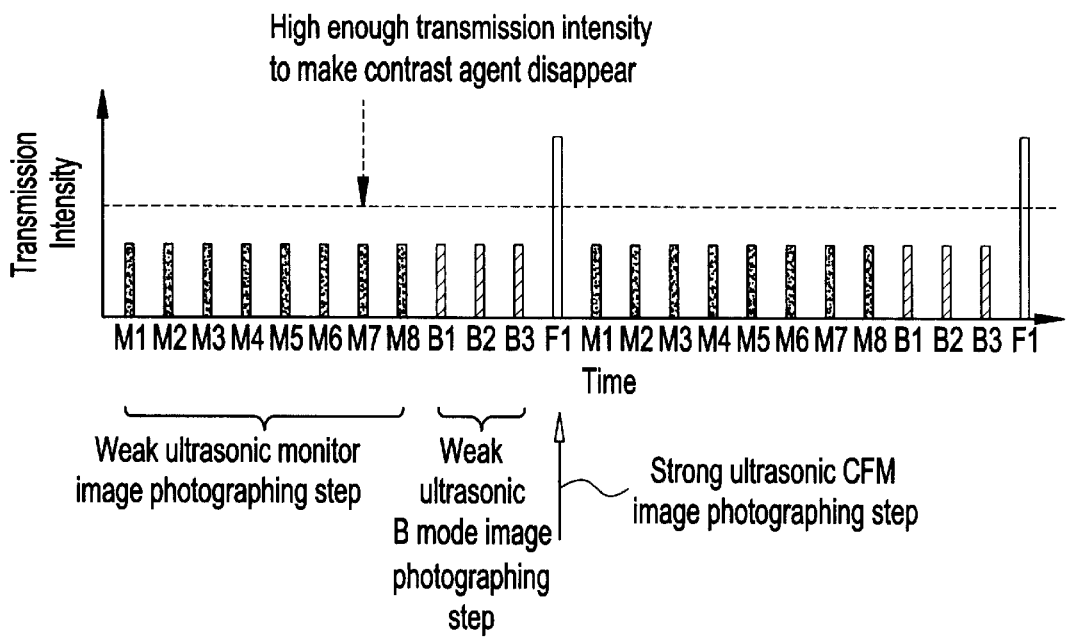
FIG. 8 is a diagram illustrating a fourth ultrasonic scanning method pertaining to the invention.

As shown in FIG. 8, the weak ultrasonic B mode image photographing step is executed immediately after the weak ultrasonic monitor image photographing step, followed by the execution of the strong ultrasonic CFM image photographing step.

Figure 9:
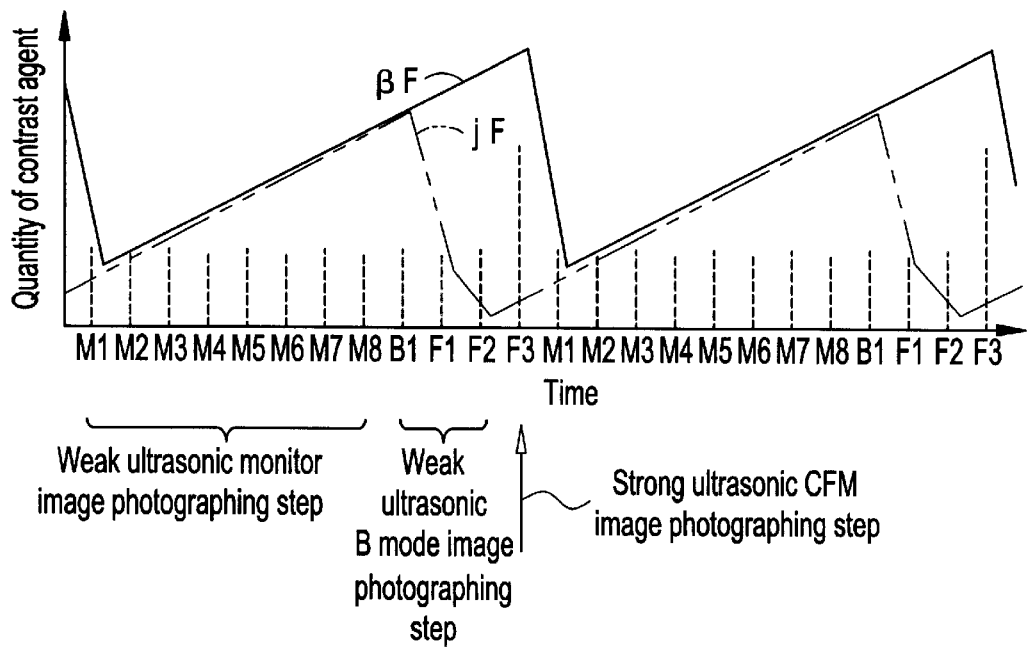
FIG. 9 is a graph showing variations in the quantity of the contrast agent in the fourth ultrasonic scanning method pertaining to the invention.

As is seen from graph βF in FIG. 9, during the weak ultrasonic monitor image photographing step and the weak ultrasonic B mode image photographing step the contrast agent increases, during the strong ultrasonic CFM mode image photographing step the contrast agent disappears, and during the weak ultrasonic monitor image photographing step and the weak ultrasonic B mode image photographing step the contrast agent increases; these variations are repeated.

As comparison of this graph βF and graph jF in the second example of the related art described above would reveal, supposing that the frame rate is the same as in the second example of the related art, the quantity of the contrast agent during the photographing of the CFM image is greater than in the second example of the related art. As a result, the picture quality of the CFM image can be improved. In other words, even if the frame rate is higher than in the second example of the related art, the quantity of the contrast agent can be kept about the same, and therefore comparable picture quality of the CFM image to that in the second example of the related art can be achieved. Thus, without sacrificing the picture quality of the CFM image, the frame rate can be raised.

The picture quality of B mode images ΣB is not so high because of the use of a weak ultrasonic wave in photographing, but the photographing in a state in the contrast agent has increased and the addition of a plurality of B mode images, their addition result in a comparable quality level to that in the second example of the related art.

Incidentally, although the picture quality of the B mode image B1 is rather poor on account of the use of a weak ultrasonic wave in photographing, it is only slightly poorer than in the second example of the related art, only the B mode image B1 can as well be used instead of using the added B mode images $\Sigma B$.

By the fourth ultrasonic scanning method so far described, BCFM-based intermittent scanning can be accomplished generally more appropriately than by the second example of the related art. Moreover it is appropriate for the observation of opacification in CFM images, and can also provide structural information through B mode images.

Fifth Ultrasonic Scanning Method

Figure 10:
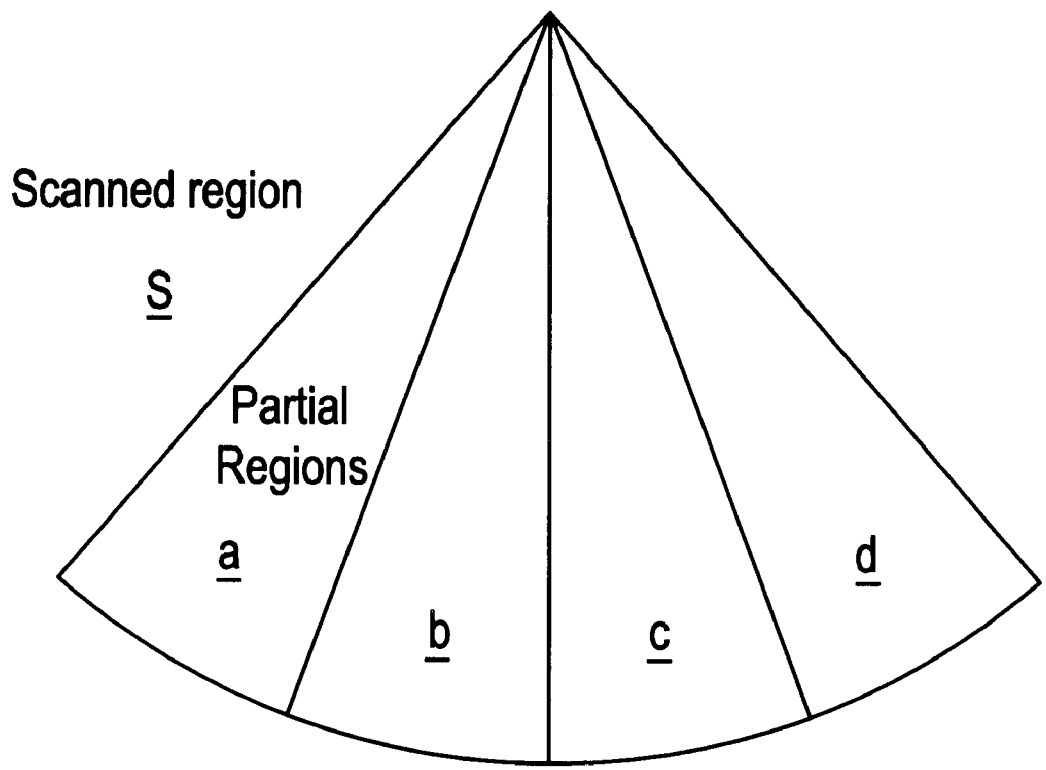
FIG. 10 is a diagram illustrating a scanned region and partial regions.

As shown in FIG. 10, the scanned region S is divided into, for instance, four partial regions a through d.

Figure 11:
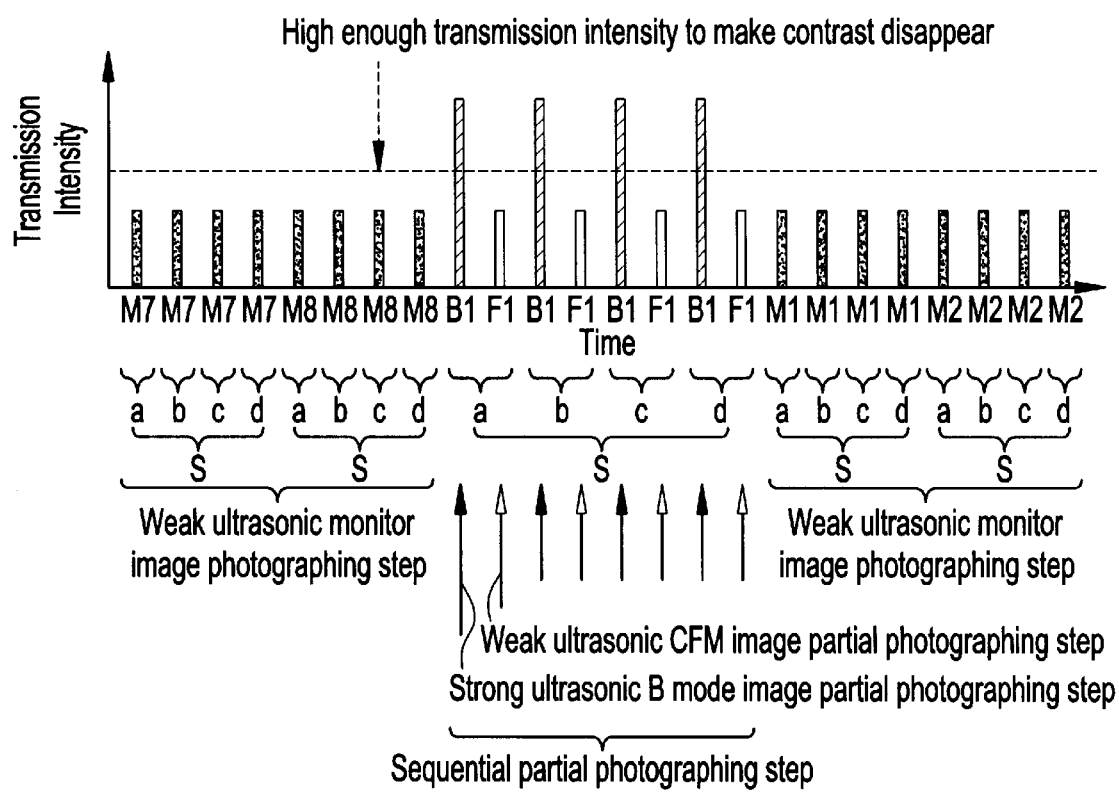
FIG. 11 is a diagram illustrating a fifth ultrasonic scanning method pertaining to the invention.

Then, as shown in FIG. 11, a photographing cycle including a weak ultrasonic monitor image photographing step of photographing monitor images M1 through M8 in the whole scanned region S by using a weak enough ultrasonic wave not to let the contrast agent disappear, and a sequential partial photographic step of sequentially performing a strong ultrasonic B mode image partial photographing step of photographing a B mode image B1 by using a strong enough ultrasonic wave to make the contrast agent disappear and a weak ultrasonic CFM image partial photographing step of photographing a CFM image F1 by using a weak enough ultrasonic wave not to let the contrast agent disappear in each of the partial regions a, b, c and d is iterated.

Figure 12:
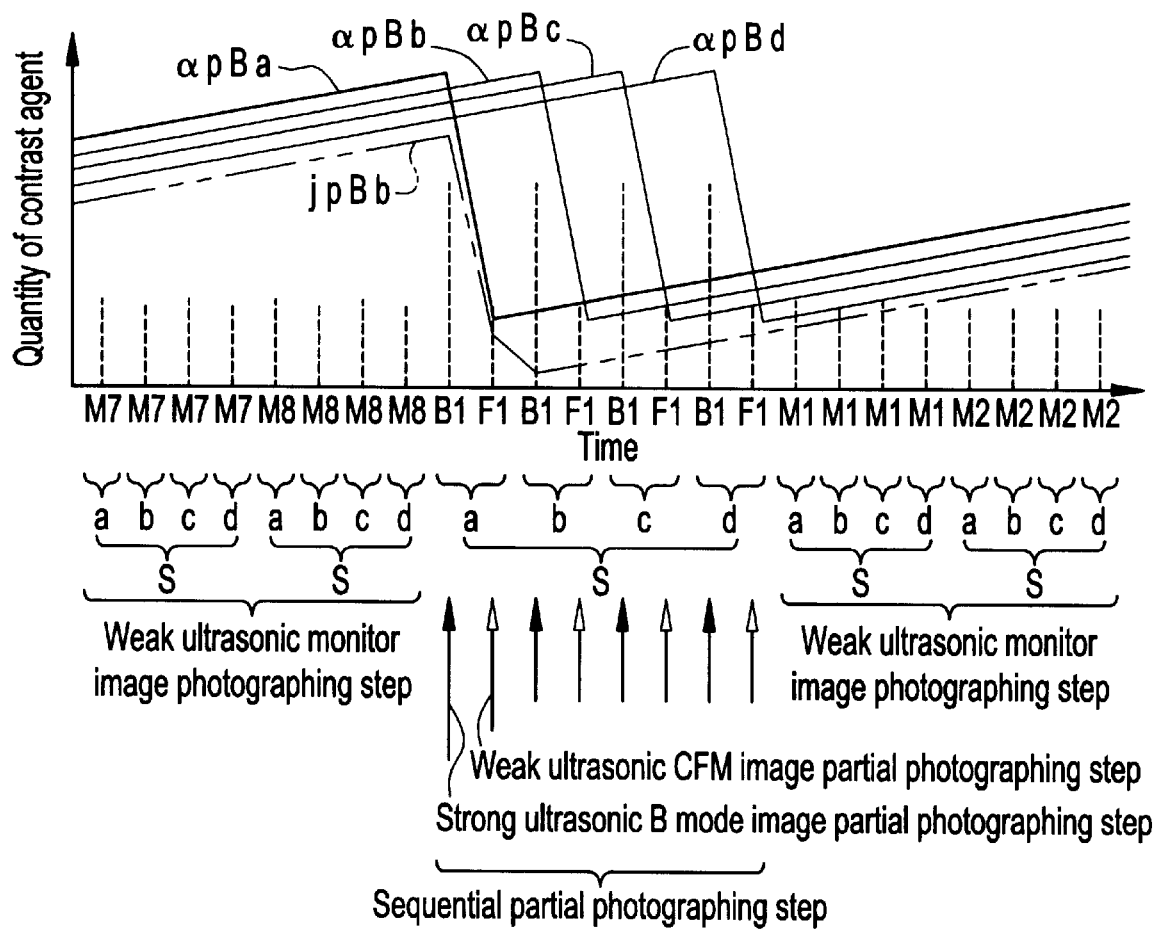
FIG. 12 is a graph showing variations in the quantity of the contrast agent in the fifth ultrasonic scanning method pertaining to the invention.

FIG. 12 is a graph showing variations in the quantity of the contrast agent present in the photographed area.

In the partial region a, as is seen from graph $\alpha pBa$, during the weak ultrasonic monitor image photographing step the contrast agent increases, and during the strong ultrasonic B mode image partial photographing step the contrast agent disappears. After that, during the weak ultrasonic CFM image partial photographing step and the weak ultrasonic monitor image photographing step the contrast agent increases, and during the strong ultrasonic B mode image photographing step the contrast agent disappears; these variations are repeated.

The same is true of graph $\alpha pBb$ of the partial region b, graph $\alpha pBc$ of the partial region c and graph $\alpha pBd$ of the partial region d as of graph $\alpha pBa$ of the partial region a.

As comparison of this graph $\alpha pBa$ and graph $jpBa$ in the third example of the related art described above would reveal, supposing that the frame rate is the same as in the third example of the related art, the quantity of the contrast agent during the photographing of the B mode image is greater than in the third example of the related art. As a result, the picture quality of the B mode image can be improved. In other words, even if the frame rate is higher than in the third example of the related art, the quantity of the contrast agent can be kept about the same, and therefore comparable picture quality of the B mode image to that in the third example of the related art can be achieved. Thus, without sacrificing the picture quality of the B mode image, the frame rate can be raised.

The picture quality of CFM image F1 is not so high on account of the photographing in a state in which much of the contrast agent has disappeared and the use of a weak ultrasonic wave, but it is only slightly poorer than in the third example of the related art.

Incidentally, as in the first ultrasonic scanning method, it is also possible to photograph a plurality of CFM images F1, F2, . . . in the partial regions, and use CFM images $\Sigma F$ resulting from their addition. These added CFM images $\Sigma F$ have about the same picture quality as in the third example of the related art.

By the fifth ultrasonic scanning method so far described, BCFM-based intermittent scanning can be accomplished generally more appropriately than by the third example of the related art. Moreover it is appropriate for the observation of opacification in B mode images, and can also provide information on blood flow in the surroundings through CFM images.

Sixth Ultrasonic Scanning Method

Figure 13:
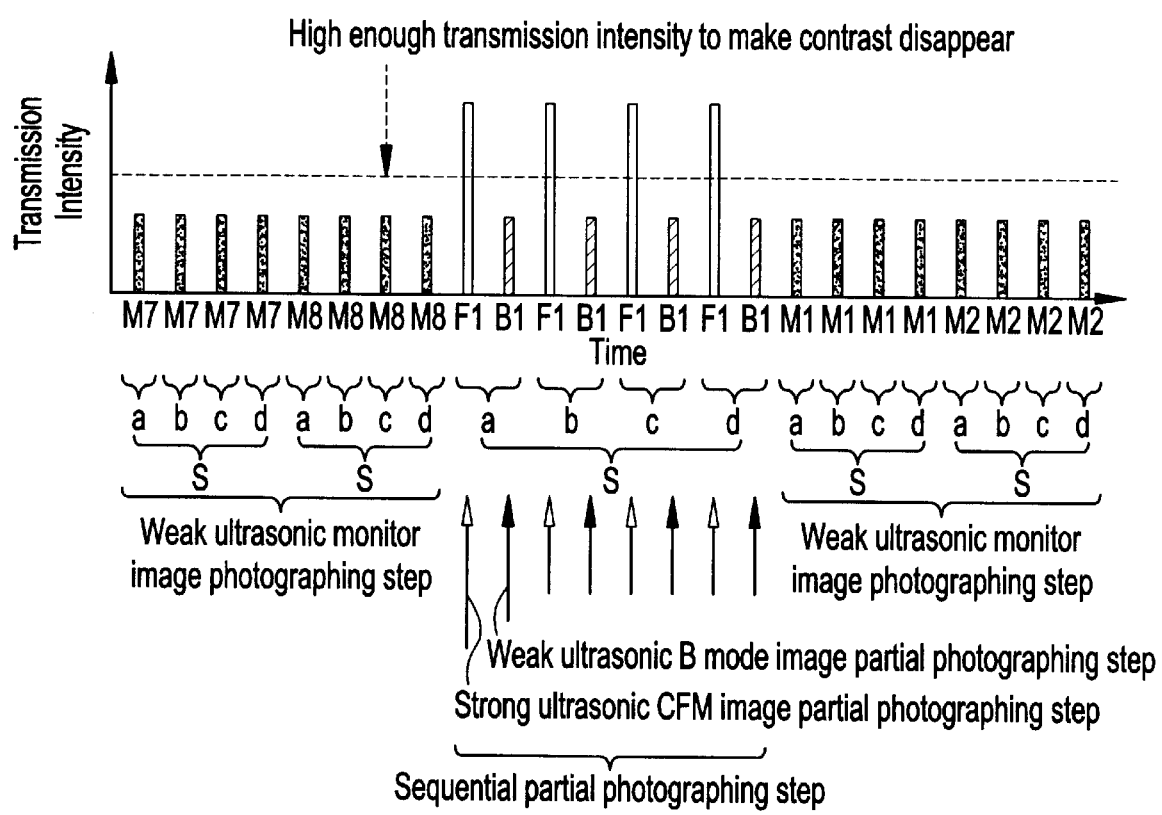
FIG. 13 is a diagram illustrating a sixth ultrasonic scanning method pertaining to the invention.

As shown in FIG. 13, a photographing cycle including a weak ultrasonic monitor image photographing step of photographing monitor images M1 through M8 in the whole scanned region S by using a weak enough ultrasonic wave not to let the contrast agent disappear, and a sequential partial photographic step of sequentially performing a strong ultrasonic CFM image partial photographing step of photographing a CFM image F1 by using a strong enough ultrasonic wave to make the contrast agent disappear and a weak ultrasonic waves B mode image partial photographing step of photographing a B mode image B1 by using a weak enough ultrasonic wave not to let the contrast agent disappear in each of the partial regions a, b, c and d is iterated.

Figure 14:
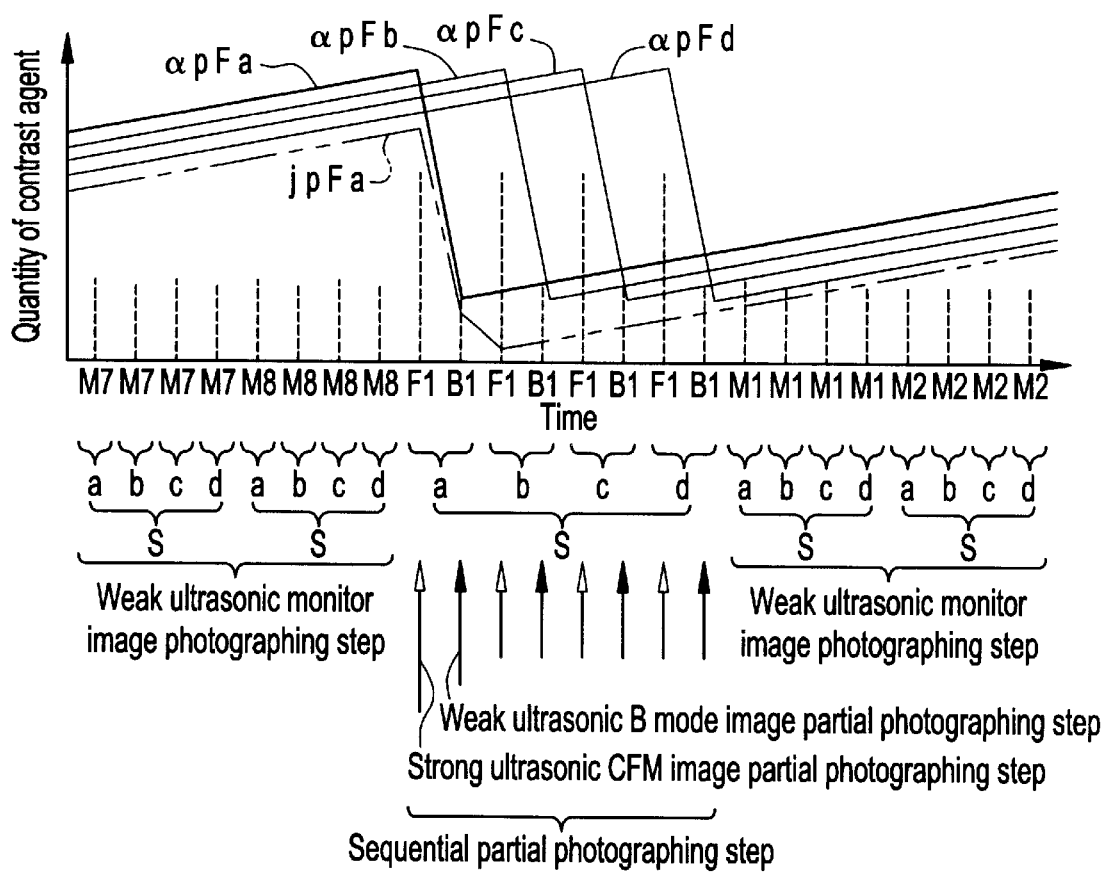
FIG. 14 is a graph showing variations in the quantity of the contrast agent in the sixth ultrasonic scanning method pertaining to the invention.

FIG. 14 is a graph showing variations in the quantity of the contrast agent present in the photographed area.

In the partial region a, as is seen from graph $\alpha pFa$, during the weak ultrasonic monitor image photographing step the contrast agent increases, and during the strong ultrasonic CFM mode image photographing step the contrast agent disappears. After that, during the weak ultrasonic B mode image photographing step and the weak ultrasonic monitor image photographing step the contrast agent increases, and during the strong ultrasonic CFM image photographing step the contrast agent disappears; these variations are repeated.

The same is true of graph $\alpha pFb$ of the partial region b, graph $\alpha PFc$ of the partial region c and graph $\alpha PFd$ of the partial region d as of graph $\alpha PFa$ of the partial region a.

As comparison of this graph $\alpha PFa$ and the fourth example of the related art described above would reveal, supposing that the frame rate is the same as in the fourth example of the related art, the quantity of the contrast agent during the photographing of the CFM image is greater than in the fourth example of the related art. As a result, the picture quality of the CFM image can be improved. In other words, even if the frame rate is higher than in the fourth example of the related art, the quantity of the contrast agent can be kept about the same, comparable picture quality of the CFM image to that in the fourth example of the related art can be achieved. Thus, without sacrificing the picture quality of the CFM image, the frame rate can be raised.

The picture quality of B mode image B1 is not so high on account of the photographing in a state in which much of the contrast agent has disappeared and the use of a weak ultrasonic wave, but it is only slightly poorer than in the fourth example of the related art.

Incidentally, as in the second ultrasonic scanning method, it is also possible to photograph a plurality of B mode images B1, BL2, . . . in the partial regions, and use B mode images $\Sigma B$ resulting from their addition. These added B mode images $\Sigma B$ have about the same picture quality as in the fourth example of the related art.

By the sixth ultrasonic scanning method so far described, BCFM-based intermittent scanning can be accomplished generally more appropriately than by the fourth example of the related art. Moreover it is appropriate for the observation of opacification in CFM images, and can also provide structural information through B mode images.

Seventh Ultrasonic Scanning Method

A seventh ultrasonic scanning method is a variation of the fifth ultrasonic scanning method in which the order of the relative positions of the strong ultrasonic B mode image photographing step and the weak ultrasonic CFM image partial photographing step are changed.

Figure 15:
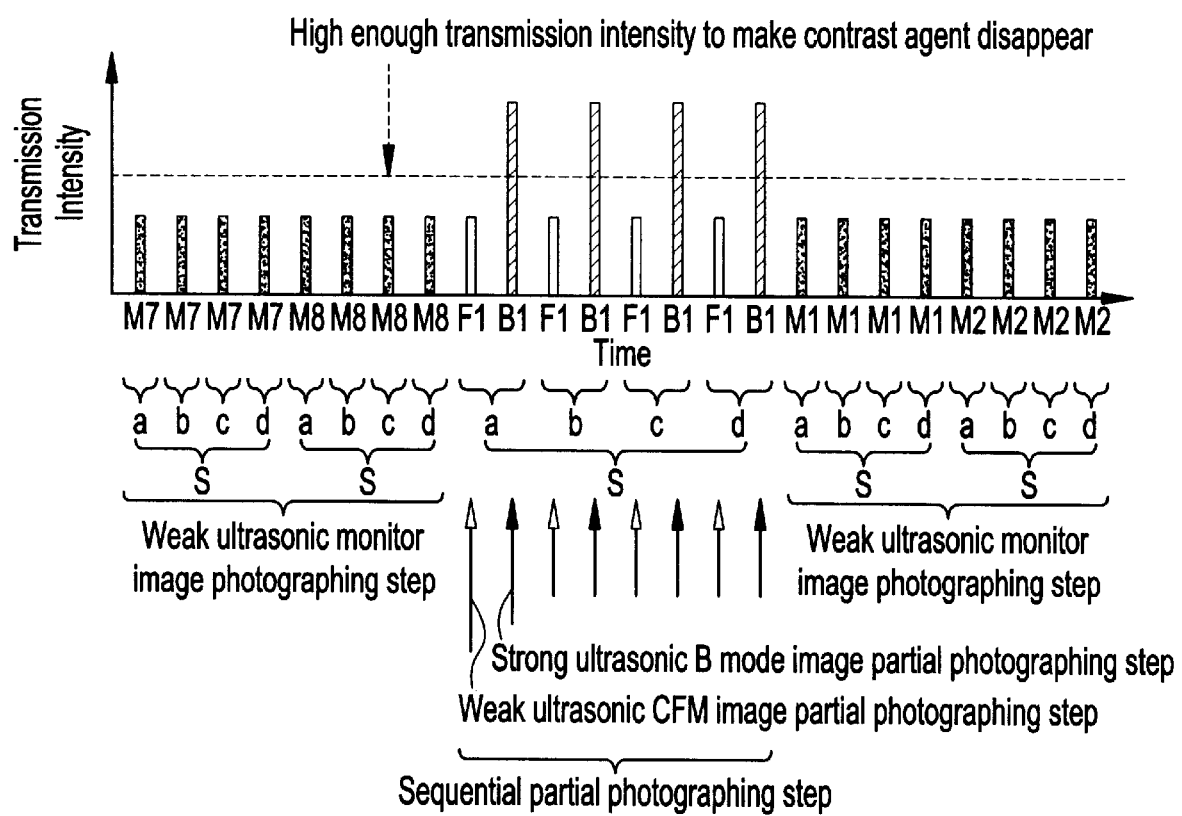
FIG. 15 is a diagram illustrating a seventh ultrasonic scanning method pertaining to the invention.

As shown in FIG. 15, the weak ultrasonic CFM image partial photographing step is executed first, followed by the execution of the strong ultrasonic B mode image photographing step.

Figure 16:
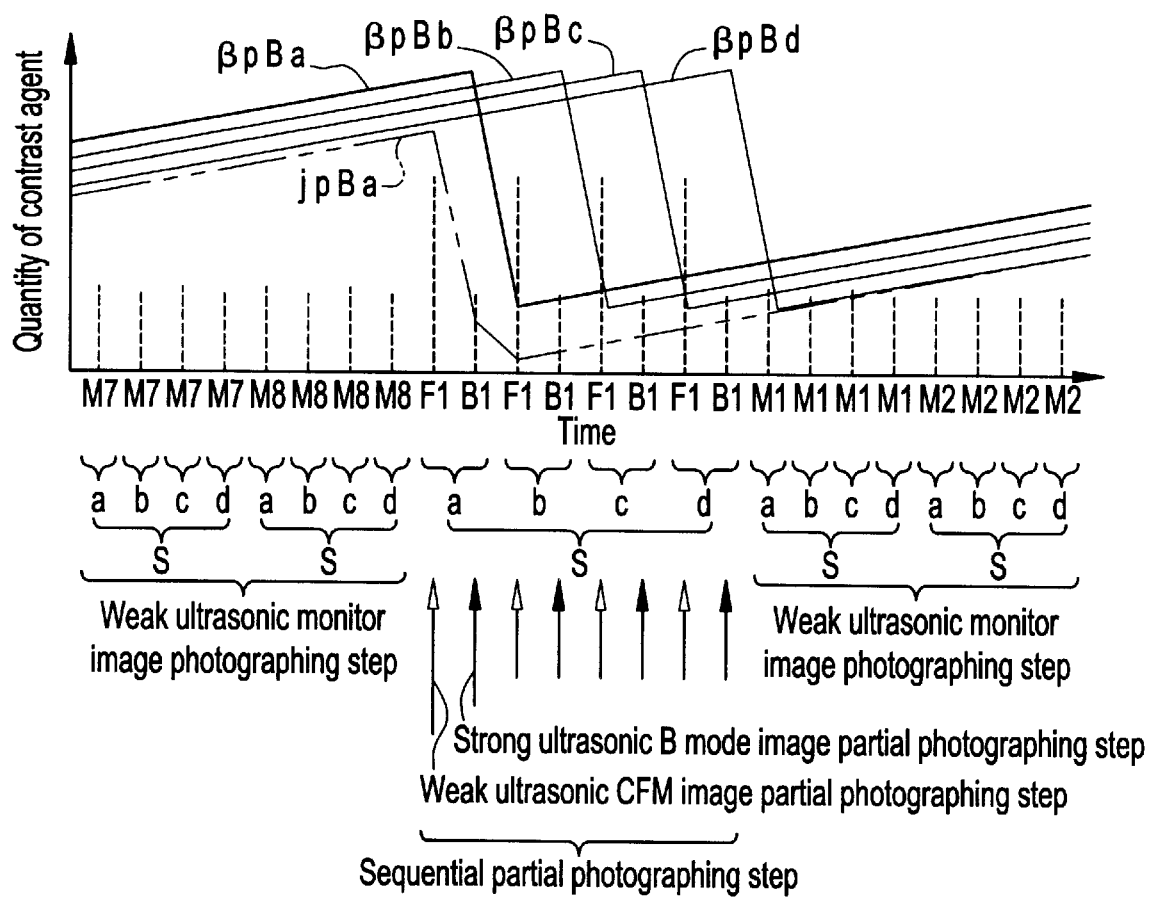
FIG. 16 is a graph showing variations in the quantity of the contrast agent in the seventh ultrasonic scanning method pertaining to the invention.

In the partial region a, as is seen from graph βPBa in FIG. 16, during the weak ultrasonic monitor image photographing step and the weak ultrasonic CFM image photographing step the contrast agent increases, during the strong ultrasonic B mode image photographing step the contrast agent disappears, and during the weak ultrasonic monitor image photographing step and the weak ultrasonic CFM image photographing step the contrast agent increases; these variations are repeated.

As comparison of this graph βPBa and graph jpBa in the third example of the related art described above would reveal, supposing that the frame rate is the same as in the third example of the related art, the quantity of the contrast agent during the photographing of the B mode image is greater than in the third example of the related art. As a result, the picture quality of the B mode image can be improved. In other words, even if the frame rate is higher than in the third example of the related art, the quantity of the contrast agent can be kept about the same, comparable picture quality of the B mode image to that in the third example of the related art can be achieved. Thus, without sacrificing the picture quality of the B mode image, the frame rate can be raised.

The picture quality of CFM image F1 is not so high on account of the use of a weak ultrasonic wave in photographing, but only slightly poorer than in the third example of the related art.

Incidentally, as in the first ultrasonic scanning method, it is also possible to photograph a plurality of CFM images F1, F2, ... in the partial regions, and use CFM images ΣF resulting from their addition. These added CFM images ΣF have about the same picture quality as in the third example of the related art.

By the seventh ultrasonic scanning method so far described, BCFM-based intermittent scanning can be accomplished generally more appropriately than by the third example of the related art. Moreover it is appropriate for the observation of opacification in B mode images, and can also provide information on blood flow in the surroundings through CFM images.

Eighth Ultrasonic Scanning Method

An eighth ultrasonic scanning method is a variation of the sixth ultrasonic scanning method in which the order of the relative positions of the strong ultrasonic CFM image photographing step and the weak ultrasonic B mode image photographing step are changed.

Figure 17:
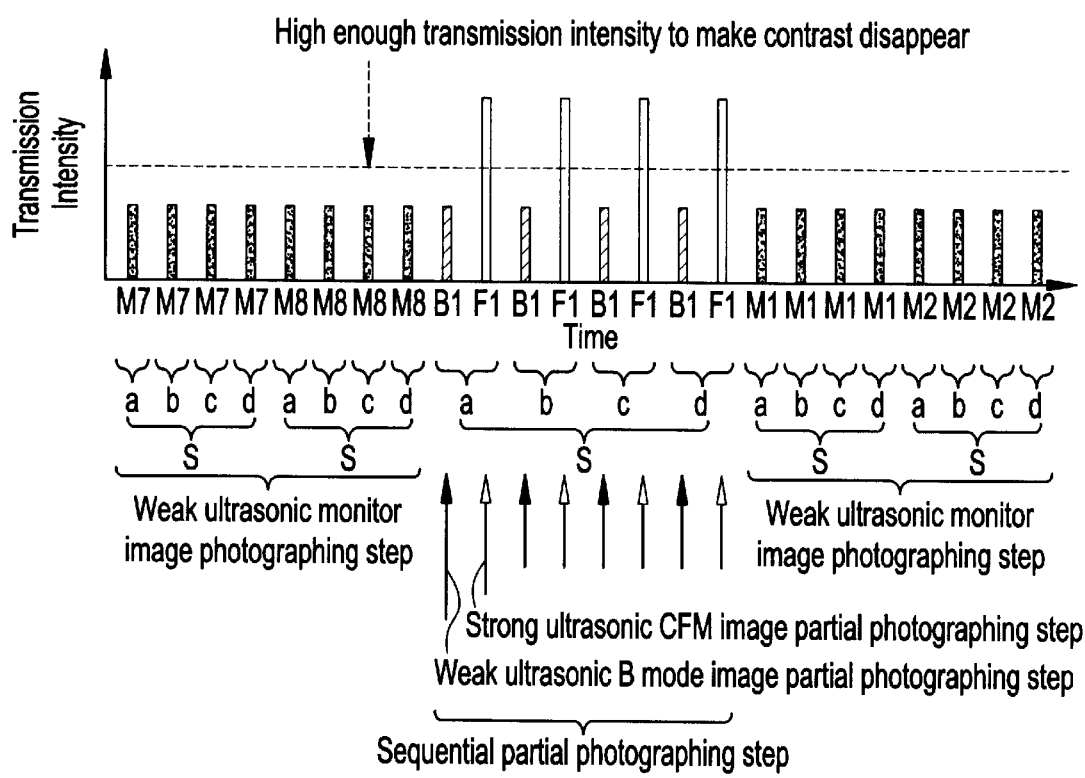
FIG. 17 is a diagram illustrating an eighth ultrasonic scanning method pertaining to the invention.

As shown in FIG. 17, the weak ultrasonic B mode image photographing step is executed first, followed by the execution of the strong ultrasonic CFM image partial photographing step.

Figure 18:
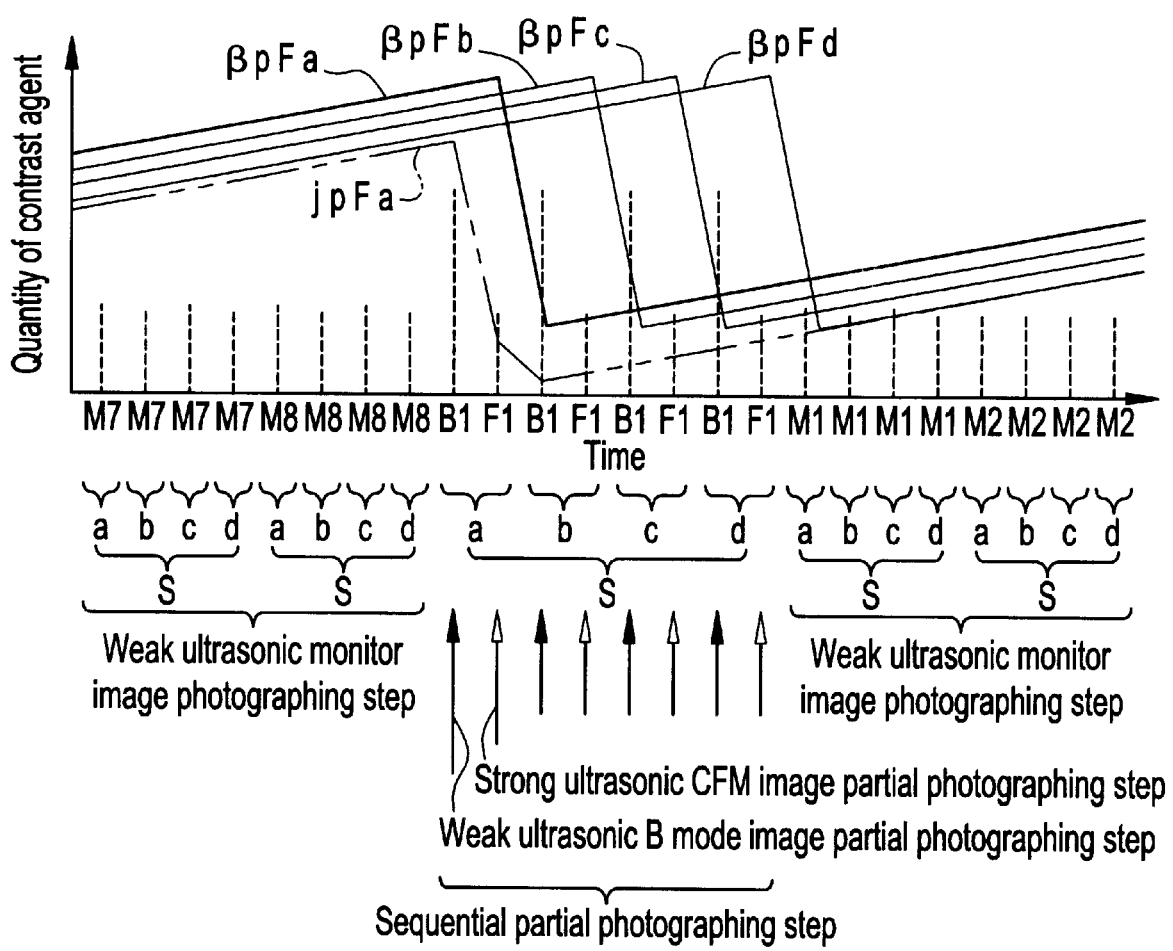
FIG. 18 is a graph showing variations in the quantity of the contrast agent in the eighth ultrasonic scanning method pertaining to the invention.
Figure 19:
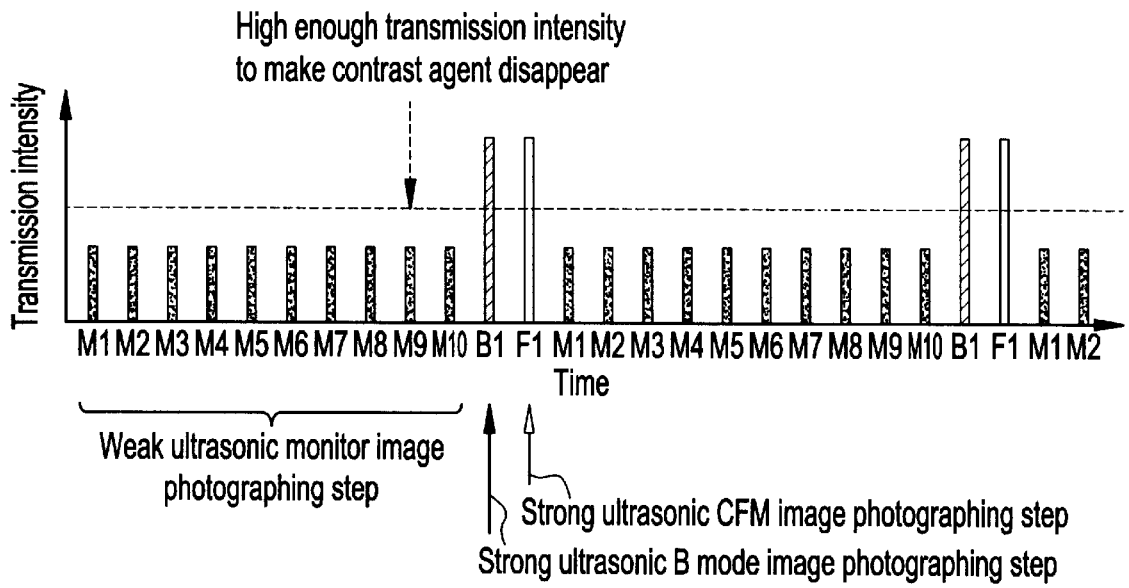
FIG. 19 is a diagram illustrating an ultrasonic scanning method, which is a first example of the related art.
Figure 20:
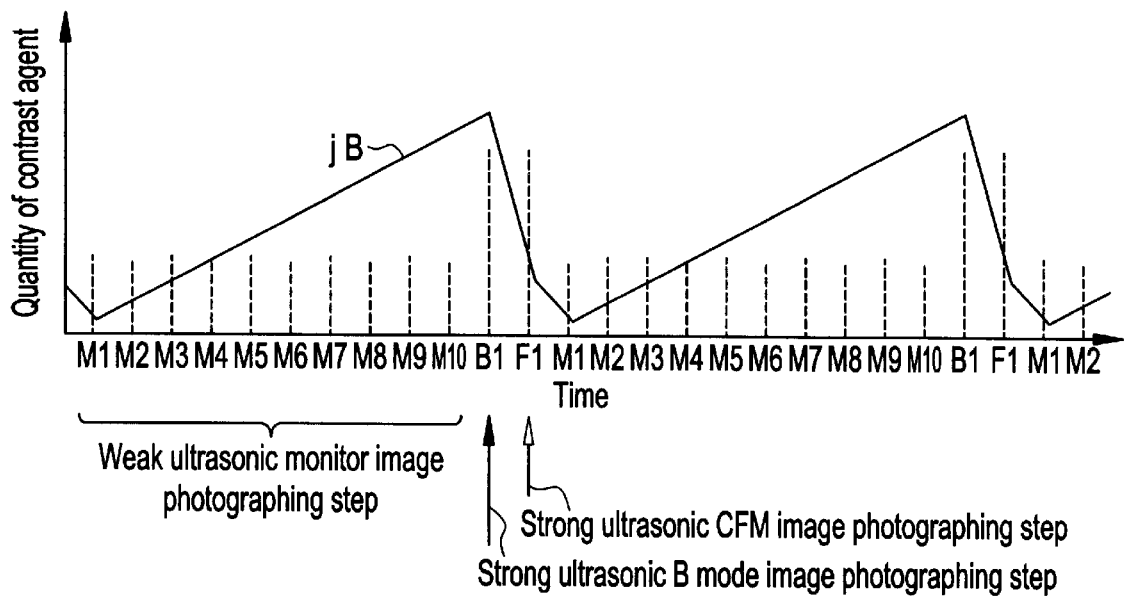
FIG. 20 is a graph showing variations in the quantity of the contrast agent in the ultrasonic scanning method, which is the first example of the related art.
Figure 21:
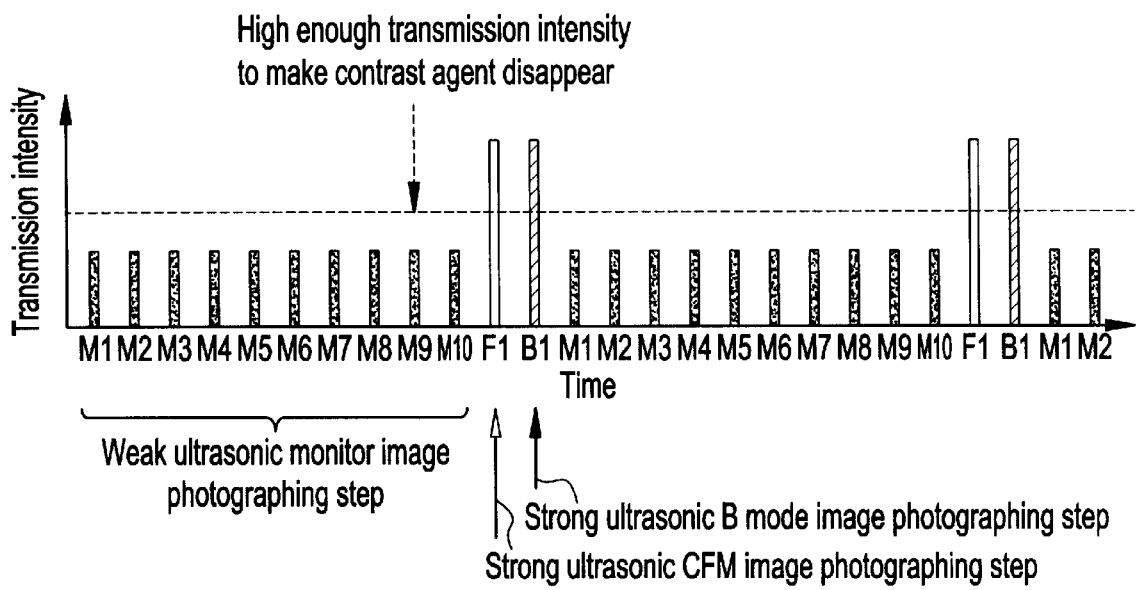
FIG. 21 is a diagram illustrating an ultrasonic scanning method, which is a second example of the related art.
Figure 22:
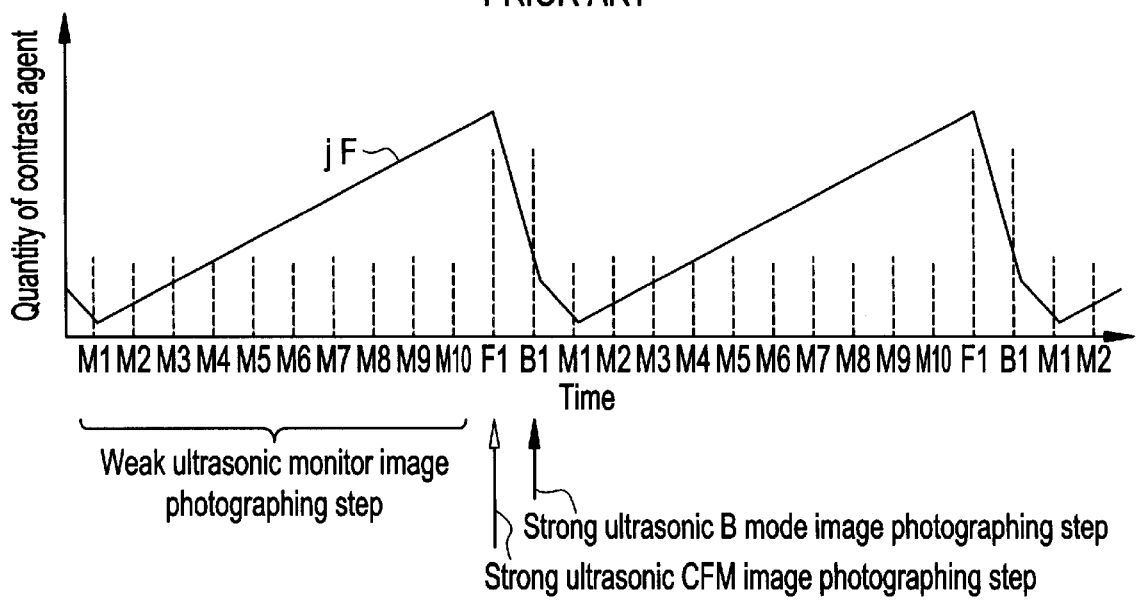
FIG. 22 is a graph showing variations in the quantity of the contrast agent in the ultrasonic scanning method, which is the second example of the related art.
Figure 23:
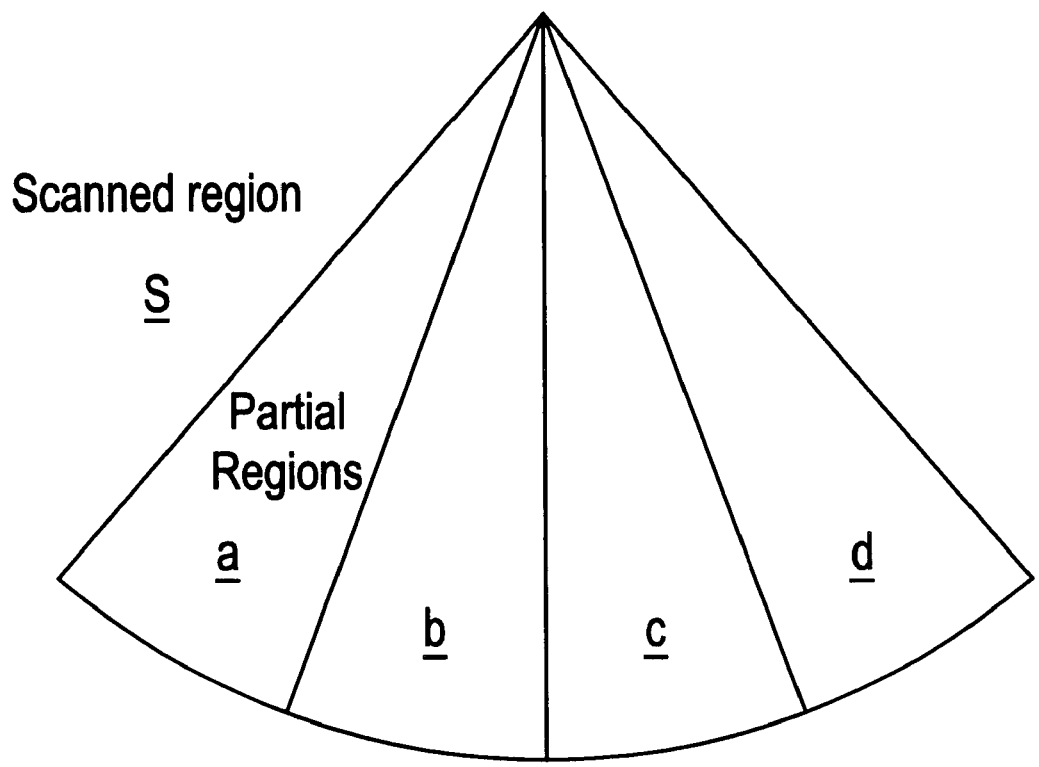
FIG. 23 is a diagram illustrating a scanned region and partial regions.
Figure 24:
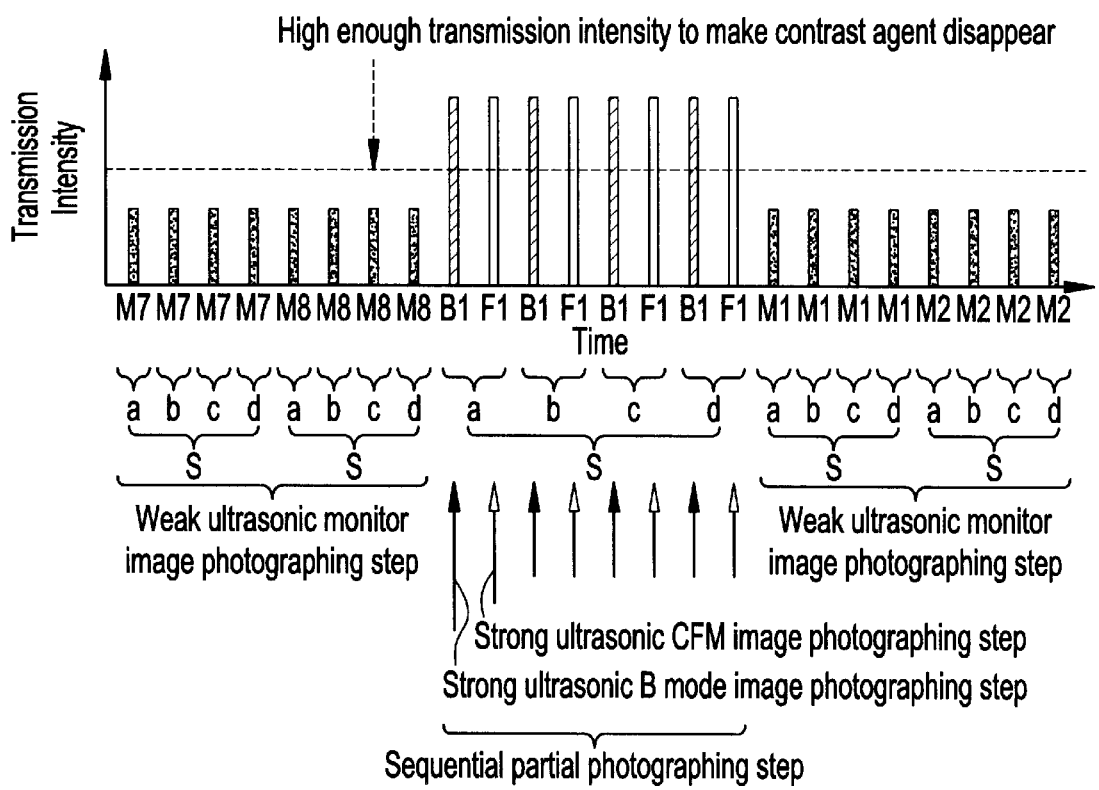
FIG. 24 is a diagram illustrating an ultrasonic scanning method, which is a third example of the related art.
Figure 25:
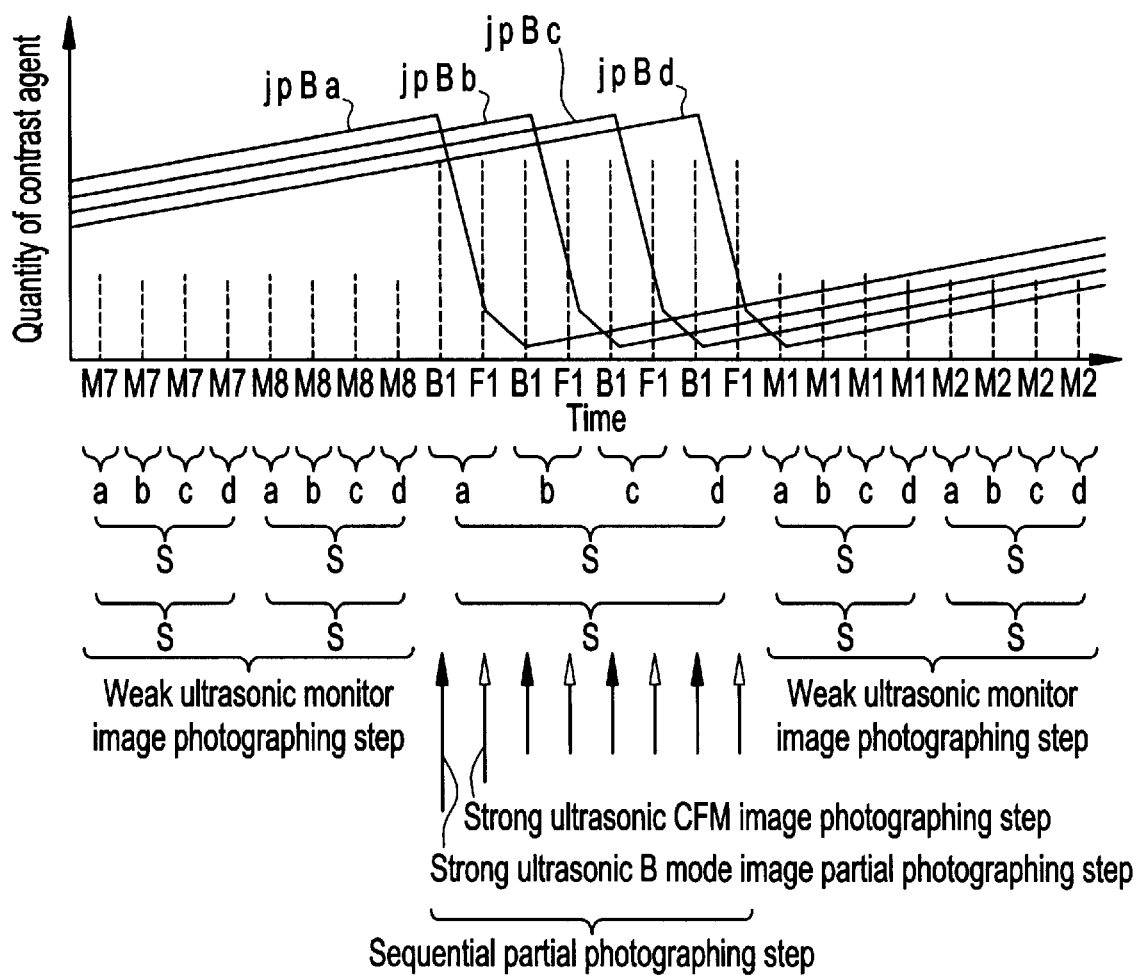
FIG. 25 is a graph showing variations in the quantity of the contrast agent in the ultrasonic scanning method, which is the third example of the related art.
Figure 26:
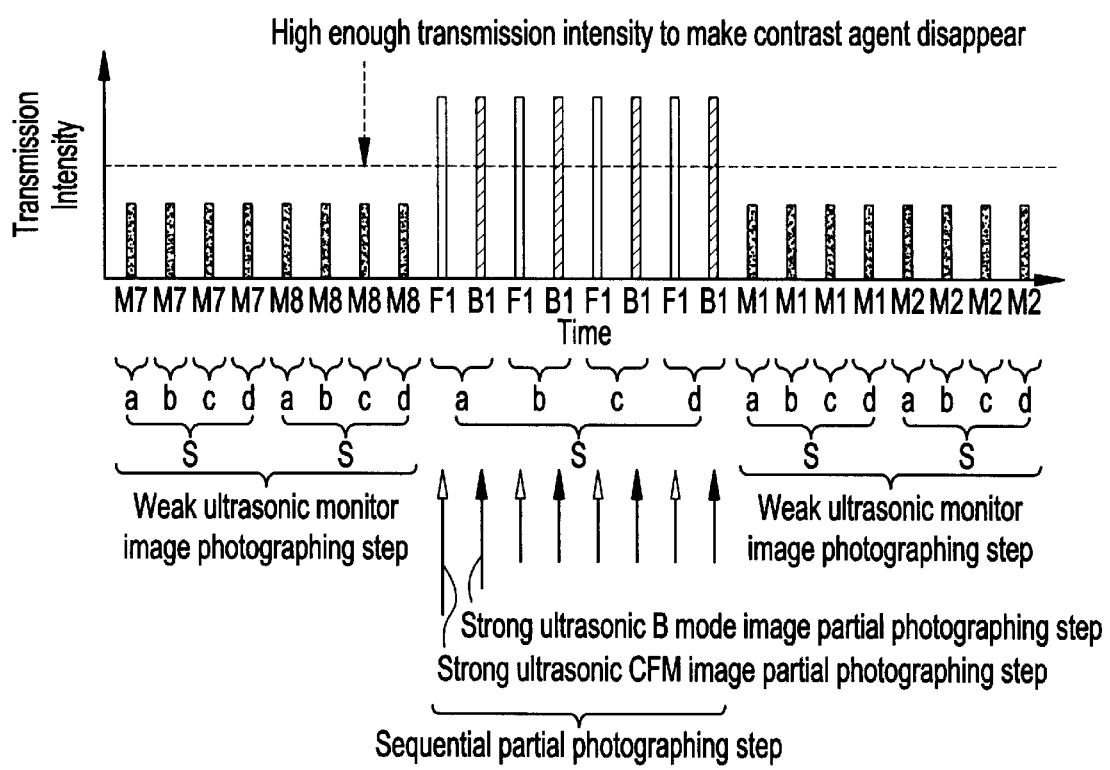
FIG. 26 is a diagram illustrating an ultrasonic scanning method, which is a fourth example of the related art.
Figure 27:
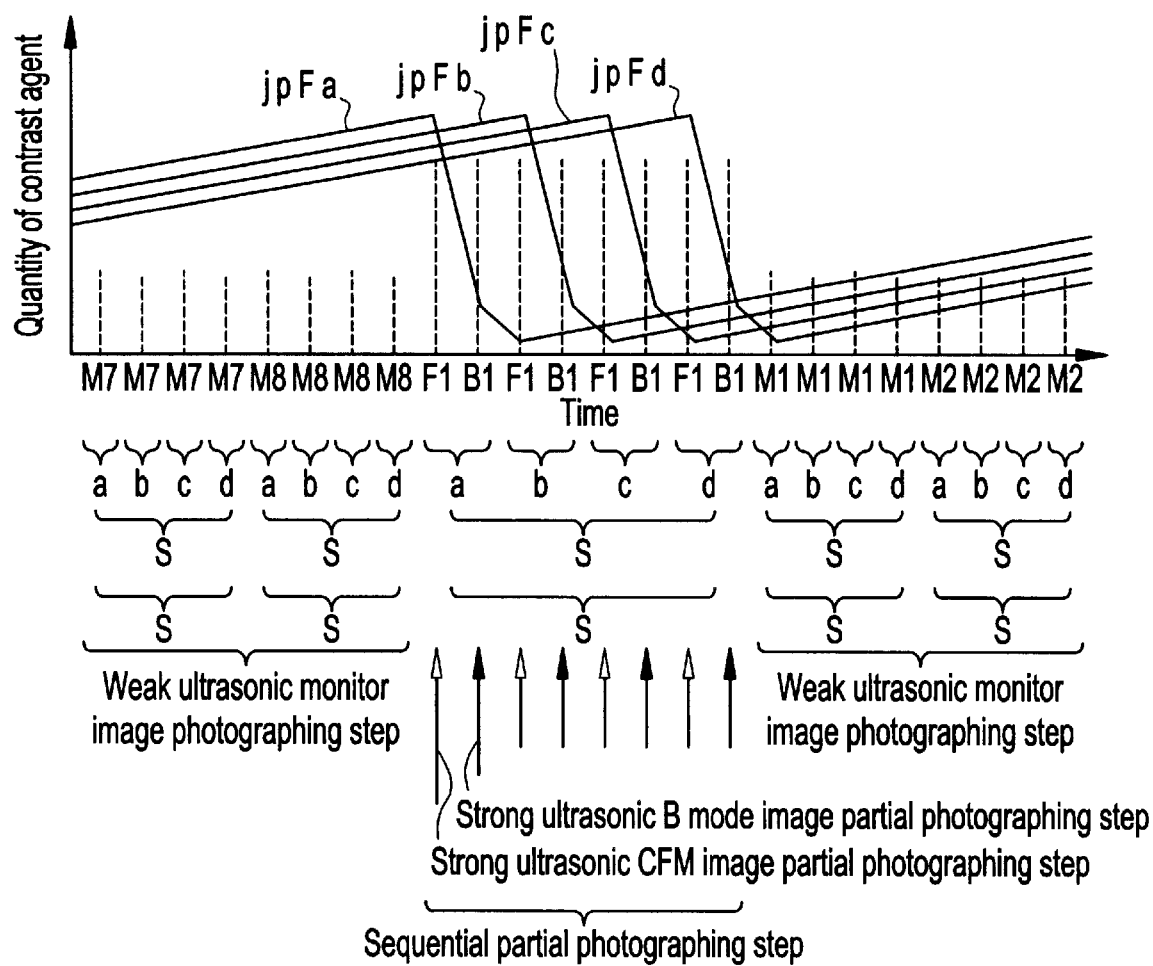
FIG. 27 is a graph showing variations in the quantity of the contrast agent in the ultrasonic scanning method, which is the fourth example of the related art.

In the partial region a, as seen from graph βpFa in FIG. 18, during the weak ultrasonic monitor image photographing step and the weak ultrasonic B mode image photographing step the contrast agent increases, during the strong ultrasonic CFM mode image photographing step the contrast agent disappears, and during the weak ultrasonic monitor image photographing step and the weak ultrasonic B mode image photographing step the contrast agent increases; these variations are repeated.

As comparison of this graph βPFa and graph jpFa in the fourth example of the related art described above would reveal, supposing that the frame rate is the same as in the fourth example of the related art, the quantity of the contrast agent during the photographing of the CFM image is greater than in the fourth example of the related art. As a result, the picture quality of the CFM image can be improved. In other words, even if the frame rate is higher than in the fourth example of the related art, the quantity of the contrast agent can be kept about the same, and therefore comparable picture quality of the CFM image to that in the fourth example of the related art can be achieved. Thus, without sacrificing the picture quality of the CFM image, the frame rate can be raised.

The picture quality of B mode image B1 is not so high on account of the photographing in a state in which much of the contrast agent has disappeared and the use of a weak ultrasonic wave, but it is only slightly poorer than in the fourth example of the related art.

Incidentally, as in the second ultrasonic scanning method, it is also possible to photograph a plurality of B mode images B1, BL2, ... in the partial regions, and use B mode images ΣB resulting from their addition. These added B mode images ΣB have about the same picture quality as in the fourth example of the related art.

By the eighth ultrasonic scanning method so far described, BCFM-based intermittent scanning can be accomplished generally more appropriately than by the fourth example of the related art. Moreover it is appropriate for the observation of opacification in CFM images, and can also provide structural information through B mode images.

As another mode of implementation, there can be cited an ultrasonic scanning method and an ultrasonic diagnostic apparatus wherein, when photographing is done by using a weak enough ultrasonic wave not to let the contrast agent disappear, a higher frequency is used than that when photographing is done by using a strong enough ultrasonic wave to make the contrast agent disappear.

As the frequency of the ultrasonic wave is raised in addition to the use of a weak ultrasonic wave, the destruction of the contrast agent can be restrained more.

Many widely different embodiments of the invention may be configured without departing from the spirit and the scope of the present invention. It should be understood that the present invention is not limited to the specific embodiments described in the specification, except as defined in the appended claims.

What is claimed is:

1. An ultrasonic diagnostic apparatus comprising an ultrasonic probe, an ultrasonic scanning device for scanning the inside of a subject by using that ultrasonic probe, an ultrasonic image generating device for generating an ultrasonic image on the basis of data obtained by scanning, and an ultrasonic image display device for displaying the ultrasonic image, wherein said ultrasonic scanning device iterates a photographing cycle comprising a strong ultrasonic B mode image photographing step of photographing B mode images by using a strong enough ultrasonic wave to make a contrast agent disappear, a weak ultrasonic turbulent image photographing step of photographing turbulent images by using a weak enough ultrasonic wave not to let the contrast agent disappear, and a weak ultrasonic monitor image photographing step of repeating many times photographing of monitor images by using a weak enough ultrasonic wave not to let the contrast agent disappear.

2. The ultrasonic diagnostic apparatus according to claim 1, wherein said ultrasonic scanning device either executes the strong ultrasonic B mode image photographing step, the weak ultrasonic turbulent image photographing step and the weak ultrasonic monitor image photographing step in this order or executes the strong ultrasonic B mode image photographing step, the weak ultrasonic monitor image photographing step and the weak ultrasonic turbulent image photographing step in this order.

3. An ultrasonic diagnostic apparatus provided with an ultrasonic probe, an ultrasonic scanning device for scanning the inside of a subject by using that ultrasonic probe, an ultrasonic image generating device for generating an ultrasonic image on the basis of data obtained by scanning, and an ultrasonic image display device for displaying the ultrasonic image, wherein said ultrasonic scanning device iterates a photographing cycle comprising a strong ultrasonic turbulent image photographing step of photographing turbulent images by using a strong enough ultrasonic wave to make a contrast agent disappear, a weak ultrasonic B mode image photographing step of photographing B mode images by using a weak enough ultrasonic wave not to let the contrast agent disappear, and a weak ultrasonic monitor image photographing step of repeating many times photographing of monitor images by using a weak enough ultrasonic wave not to let the contrast agent disappear.

4. The ultrasonic diagnostic apparatus according to claim 3, wherein said ultrasonic scanning device either executes the strong ultrasonic turbulent image photographing step, the weak ultrasonic B mode image photographing step and the weak ultrasonic monitor image photographing step in this order or the strong ultrasonic turbulent image photographing step, the weak ultrasonic monitor image photographing step and the weak ultrasonic B mode image photographing step in this order.

5. An ultrasonic diagnostic apparatus provided with an ultrasonic probe, an ultrasonic scanning device for scanning the inside of a subject by using that ultrasonic probe, an ultrasonic image generating device for generating an ultrasonic image on the basis of data obtained by scanning, and an ultrasonic image display device for displaying the ultrasonic image, wherein said ultrasonic scanning device iterates a photographing cycle comprising a sequential partial photographic step at which a scanned region is divided into two or more partial regions and a strong ultrasonic B mode partial photographing step of photographing in one partial region B mode images by using a strong enough ultrasonic wave to make the contrast agent disappear and a weak ultrasonic turbulent image partial photographing step for photographing turbulent images by using a weak enough ultrasonic wave not to let the contrast agent disappear are sequentially done for each partial region, and of a weak ultrasonic monitor image photographing step of repeating many times photographing of monitor images in the whole scanned region by using a weak enough ultrasonic wave not to let the contrast agent disappear.

6. The ultrasonic diagnostic apparatus according to claim 5, wherein said ultrasonic scanning device executes in one partial region either the strong ultrasonic B mode partial photographing step and the weak ultrasonic turbulent image photographing step in this order or the weak ultrasonic turbulent image photographing step and the strong ultrasonic B mode partial photographing step in this order.

7. The ultrasonic diagnostic apparatus according to claim 5, wherein said ultrasonic scanning device uses a higher frequency when photographing is done by using a weak enough ultrasonic wave not to let the contrast agent disappear than that when photographing is done by using a strong enough ultrasonic wave to make the contrast agent disappear.

* * * * *